(12) United States Patent
Forsell

(10) Patent No.: US 6,475,136 B1
(45) Date of Patent: *Nov. 5, 2002

(54) HYDRAULIC HEARTBURN AND REFLUX TREATMENT

(75) Inventor: Peter Forsell, Menzingen (CH)

(73) Assignee: Obtech Medical AG, Baar (CH)

( * ) Notice: Subject to any disclaimer, the term of this patent is extended or adjusted under 35 U.S.C. 154(b) by 0 days.

This patent is subject to a terminal disclaimer.

(21) Appl. No.: 09/504,047

(22) Filed: Feb. 14, 2000

(51) Int. Cl.$^7$ .................................................. A61F 2/04
(52) U.S. Cl. ..................... 600/37; 623/23.65; 623/23.67
(58) Field of Search .................. 128/897–899; 600/29–32, 37, 593; 604/27–28; 606/139–141, 151, 157, 201–203, 213, 228; 607/41; 623/23.65, 23.67

(56) References Cited

U.S. PATENT DOCUMENTS

| | | | | |
|---|---|---|---|---|
| 3,750,194 A | * | 8/1973 | Summers | 600/31 X |
| 3,875,928 A | * | 4/1975 | Angelchik | 600/37 |
| 4,246,893 A | * | 1/1981 | Berson | 128/898 |
| 4,271,827 A |   | 6/1981 | Angelchik | |
| 4,592,355 A | * | 6/1986 | Antebi | 606/144 |
| 4,696,288 A | * | 9/1987 | Kuzmak et al. | 128/898 |
| 5,006,106 A | * | 4/1991 | Angelchik | 128/898 |
| 5,042,084 A |   | 8/1991 | Daly | |
| 5,074,868 A | * | 12/1991 | Kuzmak | 606/157 |
| 5,160,338 A | * | 11/1992 | Vincent | 606/157 |
| 5,226,429 A | * | 7/1993 | Kuzmak | 128/898 |
| 5,316,543 A | * | 5/1994 | Eberbach | 128/897 |
| 5,449,368 A | * | 9/1995 | Kuzmak | 606/157 |
| 5,509,888 A | * | 4/1996 | Miller | 600/29 |
| 5,704,893 A | * | 1/1998 | Timm | 600/29 |
| 5,769,877 A | * | 6/1998 | Barreras | 607/61 |
| 5,910,149 A | * | 6/1999 | Kuzmak | 606/157 |
| 5,938,669 A | * | 8/1999 | Klaiber et al. | 606/157 |
| 5,978,712 A | * | 11/1999 | Suda et al. | 607/41 |
| 6,074,341 A | * | 6/2000 | Anderson et al. | 600/29 |

FOREIGN PATENT DOCUMENTS

| | | |
|---|---|---|
| WO | WO 00/09048 | 2/2000 |
| WO | WO 00/15158 A1 | 3/2000 |
| WO | WO 01/12078 | 8/2000 |

* cited by examiner

*Primary Examiner*—Kevin Shaver
*Assistant Examiner*—Joseph A. Cadugan
(74) *Attorney, Agent, or Firm*—Nixon & Vanderhye, P.C.

(57) ABSTRACT

A heartburn and reflux disease treatment apparatus includes an adjustable restriction device implanted in a patient and engaging the stomach close to the cardia or engaging the esophagus to form a restricted food passageway in the stomach or esophagus. An adjustment device is implanted in the patient for adjusting the restriction device to restrict and enlarge the passageway and a hydraulic operation device is implanted in the patient for operating the adjustment device. By using a wireless remote control the patient can control the hydraulic operation device, whereby the restriction device works like an artificial sphincter.

113 Claims, 12 Drawing Sheets

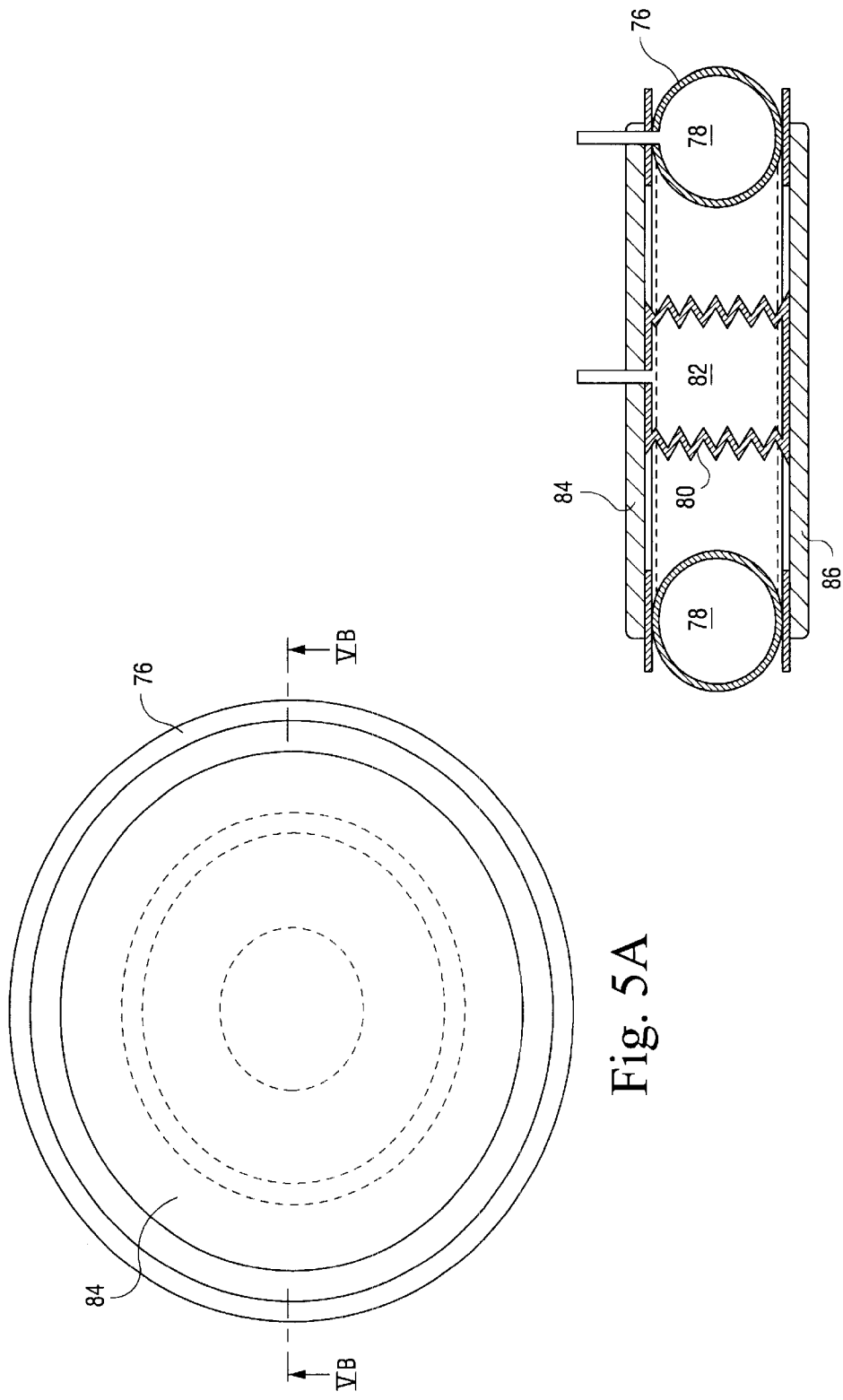

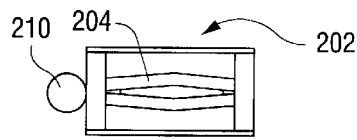
Fig. 9A
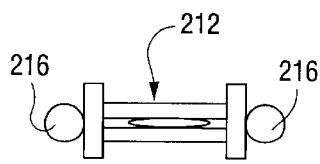
Fig. 10A
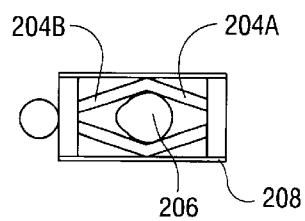
Fig. 9B
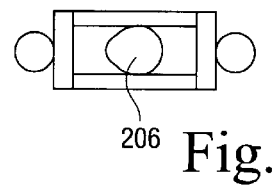
Fig. 10B
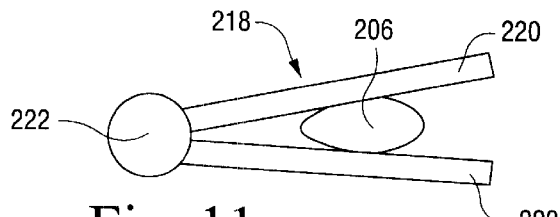
Fig. 11
Fig. 12A
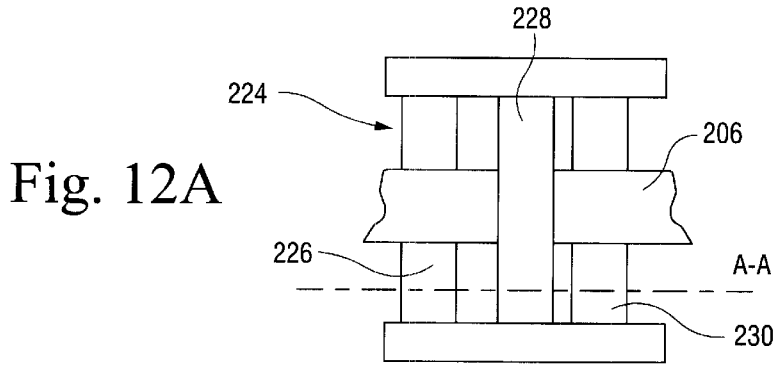
Fig. 12B
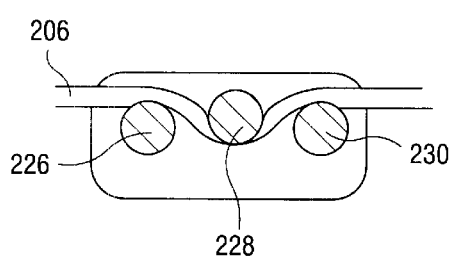
Fig. 12C
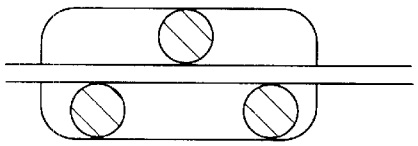

HYDRAULIC HEARTBURN AND REFLUX TREATMENT

CROSS REFERENCE TO RELATED APPLICATION

This application is based upon provisional application serial No. 60/148,345 filed Aug. 12, 1999, the disclosure of which is hereby incorporated by reference herein.

BACKGROUND OF THE INVENTION

The present invention relates to a heartburn and reflux disease treatment apparatus and method. More specifically, the invention relates to a heartburn and reflux disease treatment apparatus and method for surgical application in the abdomen of a patient for forming a restricted food passageway in the esophagus or stomach. The term "patient" includes an animal or a human being.

Chronic heartburn and reflux disease is a widespread medical problem. This is often due to hiatal hernia, i.e. a portion of the stomach immediately below the gastric fundus slides upwardly through the esophageal hiatus. In consequence, stomach acids and foods are regurgitated into the esophagus.

In the late 1970s a prior art prosthesis called Angelchik, according to U.S. Pat. No. 3,875,928, was used to operatively treat heartburn and reflux disease. However, the Angelchik prosthesis had a major disadvantage in that it was not possible to adjust the size of the restriction opening after the operation. A further disadvantage was that the prosthesis did not satisfactorily protect the esophagus and the surrounding area against injuries due to poor shape of the prosthesis. Moreover, the prosthesis was sutured to the stomach, in order to be properly positioned. Such a suture arrangement, however, is not reliable. Therefore, operations using the Angelchik prosthesis are no longer practiced.

An operation technique, semi-fundoduplicatio, is currently in use for treating heartburn and reflux disease. A most common operation is Nissen semi-fundoduplicatio, in which one takes the fundus of the stomach and makes a three quarter of a turn around the esophagus and suture between the stomach and esophagus. Although this operation works fairly well it has three main disadvantages. Firstly, most patients treated in accordance to "ad modum Nissen" lose their ability to belch. Secondly, many of these patients get dysphagia, i.e. have difficulties in swallowing after the operation. Thirdly, it is not possible to adjust the food passageway in the esophagus or stomach in any way after the operation. Characteristic for these patients is the variation of their problems over the course of a day. For example, many patients have difficulties during the night when they lie down because of stomach acid leaking up into the esophagus.

SUMMARY OF THE INVENTION

The object of the present invention is to provide a new heartburn and reflux disease treatment apparatus which permits post-operation adjustments.

Accordingly, the present invention provides a heartburn and reflux disease treatment apparatus comprising an adjustable restriction device implanted in the patient and engaging the stomach close to the cardia or engaging the esophagus to form a restricted food passageway in the stomach or esophagus, an adjustment device implanted in the patient for adjusting the restriction device to restrict and enlarge the food passageway, and a hydraulic operation device implanted in the patient for operating the adjustment device. As a result, the restriction device works like an artificial sphincter, which can be adjusted by the patient in connection with every food intake during the day, or possibly only in the morning to open up the food passageway and in the evening to close the food passageway.

Preferably the restriction device is powered and controlled in a non-manual manner. The expression "non-manually manner" should be understood to mean that the restriction device is not adjusted by manually touching subcutaneously implanted components of the apparatus or not manipulated by touching the skin of the patient. Preferably, the adjustment device adjusts the restriction device in a non-invasive manner. The expression powered should be understood as energized with everything without manual force, preferably electric energy.

The adjustment device may adjust the restriction device in a non-magnetic manner, i.e. magnetic forces may not be involved when adjusting the restriction device.

The adjustment device may also adjust the restriction device in a non-thermal manner, i.e. thermal energy may not be involved when adjusting the restriction device.

Generally the implanted restriction device comprises a holding device for preventing the region of the cardia to pass through the esophageal hiatus diaphragmatica. This could be achieved by an enlarged area of the esophagus and/or the restriction device that prevents the esophagus from passing the hole in the diaphragmatic muscle where the esophagus passes (a triangular opening surrounded by the crus muscles) or by fixing or holding the region of the cardia in place. The holding device may take the shape of a support member that provides a support for the restriction device upwardly against the diaphragm muscle. Alternatively, the holding device may comprise sutures, or the restriction device itself could be shaped to prevent the region of the cardia from sliding up. It would also be possible to provide means for narrowing the triangular opening.

In the various embodiments hereinafter described the restriction device generally forms an at least substantially closed loop. However, the restriction device may take a variety of different shapes, such as the shape of a square, rectangle or ellipse. The substantially closed loop could for example be totally flat, i.e. thin as seen in the radial direction. The shape of the restriction device may also be changed during use, be rotated or turned or moved in any direction. A physical lumen, such as the passageway in the esophagus, often is easier to restrict by contracting two opposite side walls of the lumen against each other. Thus, the restriction device may be designed to perform such a contracting effect of the opposite walls of the esophagus. Either mechanical or hydraulic solutions may be employed to operate the restriction device. Alternatively, the restriction device may comprise an adjustable cuff, a clamp or a roller for bending or rotating the esophagus or stomach to close or almost close its passageway. Such a cuff, clamp or roller may also be utilized for squeezing the esophagus against human material inside the body of the patient or against implanted structures of the apparatus. The bending or rotating members may have any shape or form and be either hydraulic or non-inflatable.

In accordance with a first main embodiment of the invention, the adjustment device comprises an expandable cavity in the restriction device, wherein the food passageway is restricted upon expansion of the cavity and enlarged upon contraction of the cavity. The cavity may change shape or form to restrict the food passageway.

The hydraulic operation device may comprise an injection port implanted subcutaneously in the patient for transcutaneously adding fluid to and withdrawing fluid from the cavity for accomplishing necessary post-operation adjustments of the restriction device to restrict or enlarge the food passageway in the esophagus or stomach. It is preferred, however, that the apparatus of the invention further comprises a reservoir implanted in the patient and containing a predetermined amount of hydraulic fluid, wherein the hydraulic operation device operates the adjustment device by using the hydraulic fluid of the reservoir. For example, the operation device may distribute hydraulic fluid from the reservoir to expand the cavity, and distribute hydraulic fluid from the cavity to the reservoir to contract the cavity, to thereby control the restriction of the passageway. As a result, there is no need for an injection port. (In certain applications, however, an injection port connected to the reservoir may be provided for enabling, normally a single once-and-for-all, calibration of the predetermined amount of fluid in the reservoir. In this case, the injection port suitably is integrated in the reservoir.)

A fluid distribution tube may readily be connected between the reservoir and the cavity in a manner so that the tube does not interfere with other implanted components of the apparatus.

Preferably, the reservoir defines a chamber for the predetermined amount of fluid and the hydraulic operation device changes the size of the chamber. The hydraulic operation device suitably comprises first and second wall portions of the reservoir, which are displaceable relative to each other to change the size of the chamber of the reservoir. The hydraulic operation device may distribute fluid from the reservoir to the cavity of the restriction member in response to a predetermined first displacement of the first wall portion of the reservoir relative to the second wall portion of the reservoir and may distribute fluid from the cavity to the reservoir in response to a predetermined second displacement of the first wall portion relative to the second wall portion.

The first and second wall portions of the reservoir may be displaceable relative to each other by manual manipulation, such as by manually pushing, pulling or rotating any of the wall portions in one direction, or alternatively, may be displaceable relative to each other by a device powered magnetically, hydraulically, or electrically (e.g. by an electric motor). In this embodiment no pump is used, only the volume of the reservoir is varied. This is of great advantage compared to the solution described below when a pump is used to pump fluid between the reservoir and the adjustment device because there is no need for a non-return valve and it is still possible to have fluid flowing both to and from the reservoir.

In accordance with a particular embodiment of the invention, the hydraulic operation, device comprises an activatable pump for pumping fluid between the reservoir and the cavity of the restriction device. The pump preferably comprises a first activation member for activating the pump to pump fluid from the reservoir to the cavity of the restriction device, and a second activation member for activating the pump to pump fluid from the cavity to the reservoir. The first and second activation members may be operable by manual manipulation thereof, such as by manually pushing, pulling or rotating any of the activation members in one direction. At least one of the activation members is constructed to operate when subjected to a predetermined external pressure.

As an alternative to the manual manipulation, at least one of the first and second activating members may be operable by a device powered magnetically, hydraulically, or electrically (e.g. by an electric motor). The pump may pump fluid both to and away from the adjustment device or hydraulic device controlling the adjustment device. A mechanical solution is proposed in which it is possible to pump in both directions just by pushing an activating member in one direction. Another alternative is a pump pumping in only one direction and an adjustable valve to change the direction of fluid to either increase or decrease the amount of fluid in the reservoir. This valve may be manipulated either manually, mechanically, magnetically, or hydraulically. Any kind of motor could be used for the different operations as well as wireless remote solutions.

Wherever a magnetic means is utilized according to the invention it may comprise a permanent magnet and a magnetic material reed switch, or other suitable known or conventional magnetic devices.

In accordance with a second main embodiment of the invention, the restriction device comprises an elongated restriction member and forming means for forming the restriction member into at least a substantially closed loop around the esophagus or stomach, the loop defining a restriction opening, whereby the adjustment device adjusts the restriction member in the loop to change the size of the restriction opening.

Advantageously, the forming means may form the restriction member into a loop having a predetermined size.

The adjustment device may change the size of the restriction opening such that the outer circumferential confinement surface of the restriction member either is changed or is unchanged.

In accordance with an embodiment of the invention, the elongated restriction member is non-inflatable and flexible, and the adjustment device pulls a first portion of the flexible restriction member from a second portion of the flexible restriction member opposite the first portion in the loop to squeeze the esophagus or stomach between two opposite lengths of the elongated flexible restriction member to restrict the passageway and releases the esophagus or stomach from the flexible restriction member to enlarge the passageway.

In accordance with a third main embodiment of the invention, the adjustment device mechanically adjusts the restriction device. Thus, the restriction device may comprise at least two elements on different sides of the esophagus or stomach, and the adjustment device may restrict the esophagus or stomach between the elements to restrict the passageway and may release the esophagus or stomach from the elements to enlarge the passageway. It is also possible to use only one element and restrict against human bone or tissue.

In accordance with an alternative, the restriction device may comprise two articulated clamping elements positioned on opposite sides of the esophagus or stomach, and the adjustment device may move the clamping elements toward each other to clamp the esophagus or stomach between the clamping elements to restrict the passageway, and may move the clamping elements away from each other to release the esophagus or stomach from the elements to enlarge the passageway.

In accordance with another alternative, the restriction device may bend a portion of the esophagus or stomach. For example, the restriction device may comprise at least two bending members, such as cylindrical or hour-glass shaped rollers, positioned on opposite or different sides of the esophagus or stomach and displaced relative to each other along the food passageway in the esophagus or stomach. The adjustment device may move the bending members against the esophagus or stomach to bend the latter to restrict the passageway, and away from the esophagus or stomach to release them from the bending members to enlarge the passageway. The bending members may have any shape or form and be both hydraulic or non-inflatable.

In accordance with another alternative aspect of the present invention there is provided two holding members, one placed more distal than the other, forming at least two substantially closed loops which may be rotated in opposite directions to each other. With interconnecting means for example flexible bands between the holding members a restriction will occur between the holding members when they are rotated.

The restriction device may in all applicable embodiments have any shape or form and be either hydraulic or non-inflatable.

In accordance with another particular embodiment of the invention, the hydraulic operation device comprises a servo means, suitably including hydraulic means. Alternatively, the servo means may include magnetic or electric means. Preferably, the servo means comprises a servo reservoir defining a chamber containing servo fluid and the hydraulic operation device comprises first and second wall portions of the servo reservoir, which are displaceable relative to each other to change the size of the chamber of the servo reservoir. The same principle will apply for the servo reservoir as for the earlier described reservoir wherein the volume in the servo reservoir may be increased or decreased by a first or second displacement of the first wall portion relative to the second wall portion of the servo reservoir and thereby control the earlier described reservoir and thereby indirectly control the cross-sectional area of the food passageway. The first and second wall portions of the servo reservoir may be displaceable relative to each other by manual manipulation, such as by manually pushing, pulling or rotating any of the wall portions of the servo reservoir in one direction. Alternatively, the first and second wall portions may be displaceable by magnetically, hydraulically or electrically powered devices. These powered devices may all be activated by manual manipulating means preferably located subcutaneously. This activation may be indirect, for example via a switch.

Especially when manual manipulation means are used, the servo means is suitable to use. With servo means less force is needed for controlling the adjustment device. Hydraulic operation is preferably used with the servo means. One example is a closed system that controls another closed system in which hydraulic components of the adjustment device are incorporated. Minor changes in the amount of fluid in a reservoir of the first system could then lead to major changes in the amount of fluid in a reservoir in the second system. Consequently, the change in volume in the reservoir of the second system affects the hydraulic operation of the adjustment device which is incorporated in the second closed system. The great advantage of such a servo means is that the larger volume system could be placed at a suitable location, e.g. inside the abdomen where there is more space, and still it would be possible to use manual manipulation means of the smaller system subcutaneously. The servo reservoir could control the reservoir of the larger volume.

The servo reservoir could be controlled directly or indirectly by a small fluid supply reservoir, which may be placed subcutaneously and may be activated by manual manipulation means controlling the servo reservoir or other suitable device.

Preferably, the hydraulic operation device comprises first and second wall portions of the fluid supply reservoir, which are displaceable relative to each other to change the size of the chamber of the fluid supply reservoir. The hydraulic operation device may distribute fluid from the fluid supply reservoir to the servo reservoir in response to a predetermined first displacement of the first wall portion of the fluid supply reservoir relative to the second wall portion of the fluid supply reservoir and to distribute fluid from the servo reservoir to the fluid supply reservoir in response to a predetermined second displacement of the first wall portion relative to the second wall portion. The wall portions of the fluid supply reservoir may be displaceable relative to each other by manual manipulation means or be displaceable relative to each other by manual manipulation means for pushing, pulling, or rotating any of the wall portions of the fluid supply reservoir in one direction. Alternatively, the wall portions of the fluid supply reservoir may be displaceable relative to each other by magnetic means, hydraulic means, manually manipulated means, or electrical control means including an electric motor. The magnetic means, hydraulic means, or electrical control means may all be activated by manually manipulated means preferably located subcutaneously. This control may be indirect, for example via a switch.

Even in the broadest embodiment of the invention the adjustment device may comprise a servo means. The servo means may comprise a hydraulic means, an electric control means, a magnetic means, mechanical means, or a manual manipulating means. The hydraulic means, electric control means, mechanical means or magnetic means may be activated by manual manipulating means. Using a servo system will save the use of force when adjusting the adjustment device which may be of importance in many applications.

The hydraulic fluid used by the operation device in any of the above embodiments may be of a kind that changes viscosity when it is exposed to energy different from thermal energy. For example, the viscosity of the hydraulic fluid may change when the fluid is exposed to electric energy. It should be understood that the word fluid also could incorporate gas or air in all embodiments.

All systems according to the invention may be controlled by a wireless remote control.

In accordance with an advantageous embodiment of the invention, there is provided a wireless remote control for non-invasively controlling the hydraulic operation device. The remote control may advantageously be capable of obtaining information on implanted components of the apparatus, in particular related to the food passageway, and of commanding the hydraulic operation device to operate the adjustment device to adjust the restriction device in response to obtained information.

The remote control comprises means for wireless transfer of energy from outside the human's or animal's body to energy consuming implanted components of the apparatus. A motor may suitably be implanted for operating the hydraulic operation device and the means for wireless transfer of energy may directly power the motor with transferred energy. The energy transferred by the means for transfer of energy may comprise wave signals, an electric field or a magnetic field.

The wireless remote control comprises an external signal transmitter, receiver or transceiver and an implanted signal receiver, transmitter or transceiver. For example, the external signal transmitter and implanted signal receiver may transmit and receive a signal in the form of digital pulses, which may comprise a magnetic or electric field. Alternatively, which is preferred, the signal transmitter and signal receiver may transmit and receive a signal, which comprises an electromagnetic wave signal, a sound wave signal or a carrier wave signal for remote control signals. The receiver may comprise a control unit for controlling the hydraulic operation device in response to a control signal from the signal transmitter.

The apparatus of the invention may further comprise an implanted energizer unit for providing energy to implanted energy consuming components of the apparatus, such as electronic circuits and/or a motor for operating the hydraulic operation device. The control unit may power such an implanted motor with energy provided by the energizer unit in response to a control signal received from the external signal transmitter. Any known or conventional signal transmitting or signal receiving device that is suitable for use with a human or mammal patient may be provided as the external signal transmitter or implanted signal receiver. The control signal may comprise an electromagnetic wave signal, such as an infrared light signal, a visible light signal, a laser light signal, a microwave signal, or a sound wave signal, such as an ultrasonic wave signal or an infrasonic wave signal, or any other type of wave signals. The control signal may also comprise electric or magnetic fields, or pulses. All of the above-mentioned signals may comprise digital signals. The control signal may be carried by a carrier signal, which may be the same as the wireless energy signal. Preferably, a digital control signal may be carried by an electromagnetic wave signal. The carrier signal or control signal may be amplitude or frequency modulated.

The motor may be any type of motor, such as a pneumatic, hydraulic or electric motor and the energizer unit may power the motor with pressurized gas or liquid, or electric energy, depending on the type of motor. Where the motor is an electric motor, it may power pneumatic or hydraulic equipment.

The energizer unit may comprise a power supply and the control unit may power the motor with energy from the power supply. Preferably, the power supply is an electric power supply, such as a battery, and the motor is an electric motor. In this case, the battery also continuously powers the circuitry of the signal receiver between the adjustment operations, in order to keep the signal receiver prepared for receiving a signal transmitted from the signal transmitter.

The energizer unit may transfer energy from the control signal, as the latter is transmitted to the signal receiver, into electric energy for powering the implanted electronic components. For example, the energizer unit may transfer the energy from the control signal into direct or alternating current.

In case there is an implanted electric motor for operating the hydraulic operation device the energizer unit may also power the motor with the transferred energy. Advantageously, the control unit directly powers the electric motor with electric energy, as the energizer unit transfers the signal energy into the electric energy. This embodiment is particularly simple and does not require any recurrent invasive measures for exchanging empty power supplies, such as batteries, that is required in the first embodiment described above.

For adjustment devices of the type that requires more, but still relatively low, power for its operation, the energizer unit may comprise a rechargeable electric power supply for storing the electric energy obtained and the control unit may power the electric motor with energy from the rechargeable electric power supply in response to a control signal received from the signal transmitter. In an initial charging step the rechargeable power supply can be charged over a relatively long time (e.g. a few seconds up to a half hour) without powering the electric motor. In a following operating step, when the power supply has been charged with sufficient energy, the control unit powers the electric motor with energy from the charged power supply to operate the hydraulic operation device, so that a desired change of the cross-sectional area of the food passageway is achieved. If the capacity of the power supply is insignificant to achieve the necessary adjustment in one single operating step, the above steps may conveniently be repeated until the desired adjustment is achieved.

The electric power supply suitably comprises an inexpensive simple capacitor. In this case, the electric motor may be a stepping motor.

The signal transmitter may transmit an electromagnetic control signal and the energizer unit may draw radiant energy from the electromagnetic wave signal, as the latter is transmitted to the signal receiver, and may transfer the radiant energy into electric energy. Alternatively, the energizer unit may comprise a battery, an electrically operable switch for connecting the battery to the signal receiver in an on mode when the switch is powered and for keeping the battery disconnected from the signal receiver in a standby mode when the switch is unpowered, and a rechargeable electric power supply for powering the switch. The control unit may power the electric motor with energy from the battery in response to a control signal received from the signal transmitter, when the switch is in its on mode. Advantageously, the energizer unit may transfer wave energy from the control signal, as the latter is transmitted to the signal receiver, into a current for charging the rechargeable electric power supply, which suitably is a capacitor. Energy from the power supply is then used to change the switch from off (standby mode) to on. This embodiment is suited for adjustment devices of the type that require relatively high power for their operation and has the advantage that the electronic circuitry of the signal receiver does not have to be powered by the battery between adjustment operations. As a result, the life-time of the battery can be significantly prolonged. The switch may also be mechanically, manually or magnetically operated. Preferable the switch is controlled by wireless energy.

As an example, the signal transmitter may transmit an electromagnetic wave signal and the energizer unit may draw radiant energy from the electromagnetic wave signal, as the latter is transmitted to the signal receiver, and may transfer the radiant energy into electric current. The energizer unit suitably comprises a coil of the signal receiver for inducing an alternating current as the electromagnetic wave signal is transmitted through the coil and a rectifier for rectifying the alternating current. The rectified current is used for charging the rechargeable power source.

Alternatively, the signal transmitter and receiver may solely be used for control signals and a further signal transmitter and signal receiver may be provided for transferring signal energy to implanted components. By such a double system of signal transmitters and receivers the advantage is obtained that the two systems can be designed optimally for their respective purposes, namely to transmit control signals and to transfer energy from signals.

A control device for controlling the restriction device may conveniently be provided and may comprise an internal programmable control unit implanted in the patient and, possibly an external control unit outside the patient's body for programming the programmable internal control unit. Alternatively, the external control unit may be programmable and wirelessly control the restriction device. At least one sensor for sensing at least one physical parameter of the patient may conveniently be implanted in the patient. The sensor may sense the pressure against the restriction device or the colon or rectum or other important parameters. Either the internal control unit or the external control unit of the control device may suitably control the restriction device to release the fecal passage way. For safety the restrictor device may release the fecal passageway in response to the sensor sensing for example an abnormally high pressure. The internal control unit may directly controls the restriction device in response. to signals by the sensor.

The apparatus preferably comprises a control device having an internal and/or an external control unit for controlling the restriction device preferably for wirelessly controlling the restriction device. Preferably the implanted internal control unit is programmable by the external control unit. The external control unit may also be programmable.

The adjustment device or other energy consuming components of the apparatus may also be energized with wirelessly transmitted energy from outside the patient's body or with an implanted battery or accumulator.

The apparatus may further comprise an implanted energy transfer device, wherein the control device releases electric energy and the energy transfer device transfers the electric energy direct or indirect into kinetic energy for operation of the restriction device.

The apparatus according may further comprise a pressure sensor for directly or indirectly sensing the pressure against the restriction device or other important parameters of the patient or the heartburn and reflux disease apparatus and the control device may control the restriction device in response to signals from the pressure sensor. The adjustment device preferably non-invasively adjusts the restriction device to change the size of the cross-sectional area.

In all applications a motor may be operatively connected to the adjustment device. A reversing device may control the motor and may be implanted in the patient for reversing the motor. The reversing device implanted in the patient may also reverse the function performed by the restriction device.

The adjustment device preferably in all embodiments adjusts the restriction device in a non-manual manner.

It should be understood that all the applicable embodiments in this application may be combined to achieve alternative embodiments of the invention.

The above described embodiments according to the general aspect of the invention may also be implemented in the described embodiments according to the alternative aspects of the invention, where applicable.

The invention also relates to a method of treating a human or animal having heartburn and reflux disease, comprising (a) Surgically implanting in the abdomen of the human or animal an adjustable restriction device which restricts a food passageway in the stomach close to the cardia or in the esophagus. And (b) from time to time, adjusting the restriction device so as (i) to enlarge the restricted passageway to allow food to readily pass therethrough into the human's or animal's stomach, or to allow the human or animal to regurgitate, or (ii) to restrict the restricted passageway sufficiently so as to substantially prevent regurgitation of stomach acids and foods into the esophagus. The restriction device may comprise a cavity which is expandable and contractable by the supply of hydraulic fluid thereto, wherein (a) is practiced in part by implanting in the human or animal a reservoir containing a predetermined amount of hydraulic fluid and connecting the reservoir to the cavity and a hydraulic operation device for distributing fluid from the reservoir to the cavity, and wherein (b) is practiced by controlling the hydraulic operation device from a point outside the human's or animal's body without physically penetrating the human's or animal's body.

In accordance with one alternative, the restriction device may comprises a cavity which is expandable and contractable by the supply of hydraulic fluid thereto, wherein (a) is practiced in part by subcutaneously implanting in the human or animal an injection port connected to the cavity of the restriction device, and wherein (b) is practiced by injecting fluid through the injection port to expand the cavity to restrict the passageway and by withdrawing fluid from the injection port to contract the cavity to enlarge the passageway.

In accordance with another alternative, the restriction device is acted upon by an adjustment device which mechanically adjusts the restriction of the food passageway; wherein (a) is practiced in part by implanting in the human or animal the adjustment device, implanting a reservoir containing a predetermined amount of hydraulic fluid and connecting the reservoir to the cavity, and implanting a hydraulic operation device for distributing fluid from the reservoir to the cavity; and wherein (b) is practiced by controlling the hydraulic operation device from a point outside the human or animal's body without physically penetrating the human's or animal's body to control the adjustment device so that the restriction of the food passageway is changed.

In accordance with yet another alternative, (a) is practiced by: (i) inflating the human's or animal's abdomen with gas by penetration of the human's or animal's skin, (ii) introducing at least two laparascopic trocars into the abdomen to introduce the restriction device and one or more medical instruments, and then (iii) applying the restriction device on the esophagus or stomach.

The invention also relates to a further method of treating a human or animal having heartburn and reflux disease, comprising (a) Surgically implanting in the abdomen of the human or animal an adjustable restriction device which restricts a food passageway in the stomach close to the cardia or in the esophagus. And (b) from time to time, adjusting the restriction device so as (i) to enlarge the restricted passageway to allow food to readily pass therethrough into the human's or animal's stomach, or to allow the human or animal to regurgitate, or (ii) to restrict the restricted passageway sufficiently so as to substantially prevent regurgitation of stomach acids and foods into the esophagus.

The invention also relates to yet a further method of treating a human or animal having heartburn and reflux disease, comprising the steps of: (a) Laparascopically placing a restriction device of the apparatus through the abdomen or thorax of a the human or animal. (b) Placing at least two laparoscopic trocars within the human's or animal's body. (c) Using a dissecting tool inserted through the laparoscopic trocar, dissecting the region of the esophagus or stomach. (d) Introducing the restriction device through the trocars. (e) Placing the restriction device in engagement with the esophagus or the upper part of the stomach to create a restricted stoma. And (f) from time to time, adjusting the restriction device so as (i) to enlarge the restricted stoma to allow food to readily pass therethrough into the human's or animal's stomach, or to allow the human or animal to regurgitate, or (ii) to restrict the restricted stoma sufficiently so as to substantially prevent regurgitation of stomach acids and foods into the esophagus.

BRIEF DESCRIPTION OF THE DRAWINGS

FIG. 5A is a perspective view of a hydraulic, pneumatic or mechanical servo system in accordance with a particular embodiment of the principal embodiment shown in FIG. 1D.

FIG. 5B is a cross-sectional view taken along line VB—VB of FIG. 5A.

FIGS. 9A and 9B are schematic views of a first mechanical restriction device for use in accordance with the invention;

FIGS. 10A and 10B are schematic views of a second mechanical restriction device for use in accordance with the invention;

FIG. 11 is a schematic view of a third mechanical restriction device for use in accordance with the invention;

FIG. 12A is a schematic front view of a fourth mechanical restriction device for use in accordance with the invention;

FIGS. 12B and 12C are sectional views along the line A—A of FIG. 12A;

DETAILED DESCRIPTION OF THE DRAWINGS

Figure 1A:
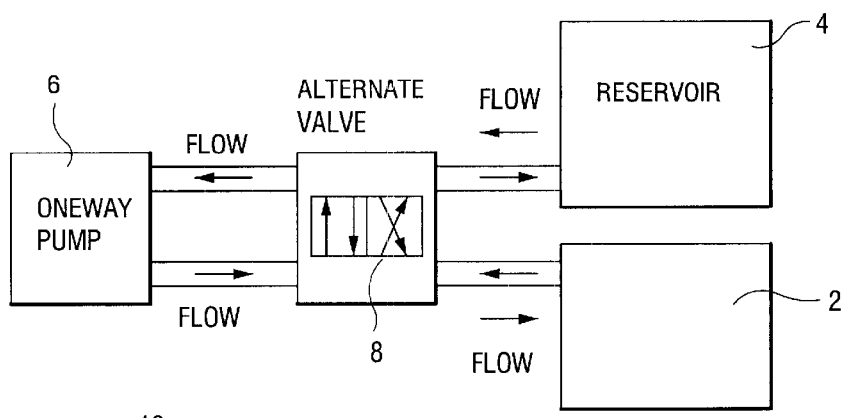
FIGS. 1A–D are block diagrams of four different principal embodiments of the heartburn and reflux disease treatment apparatus according to the invention.

Referring to the drawing figures, like reference numerals designate identical or corresponding elements throughout the several figures.

Figure 1B:
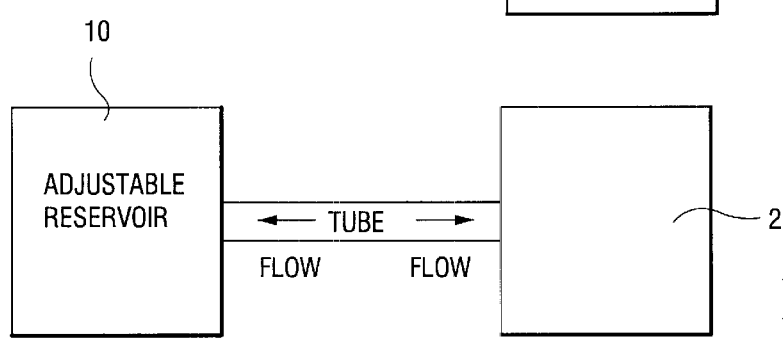
Figure 1C:
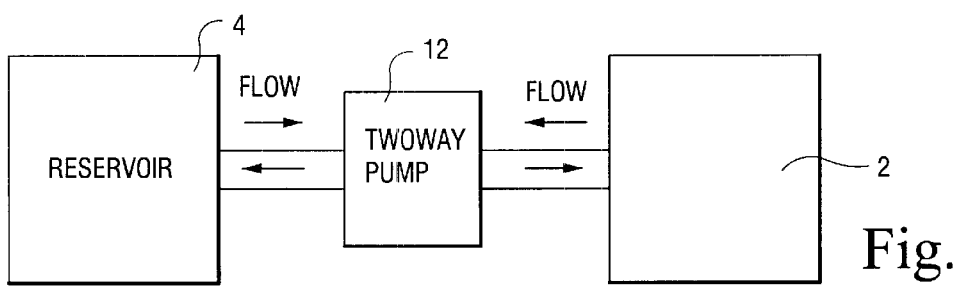
Figure 1D:
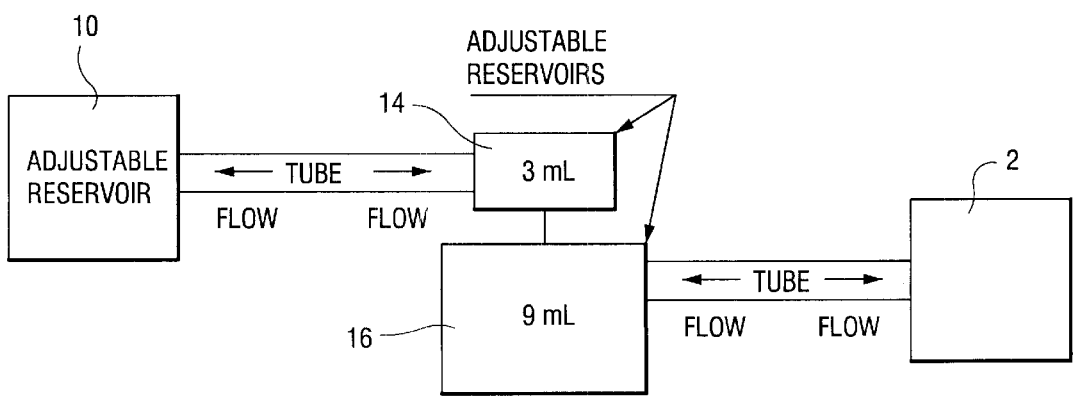
Figure 8:
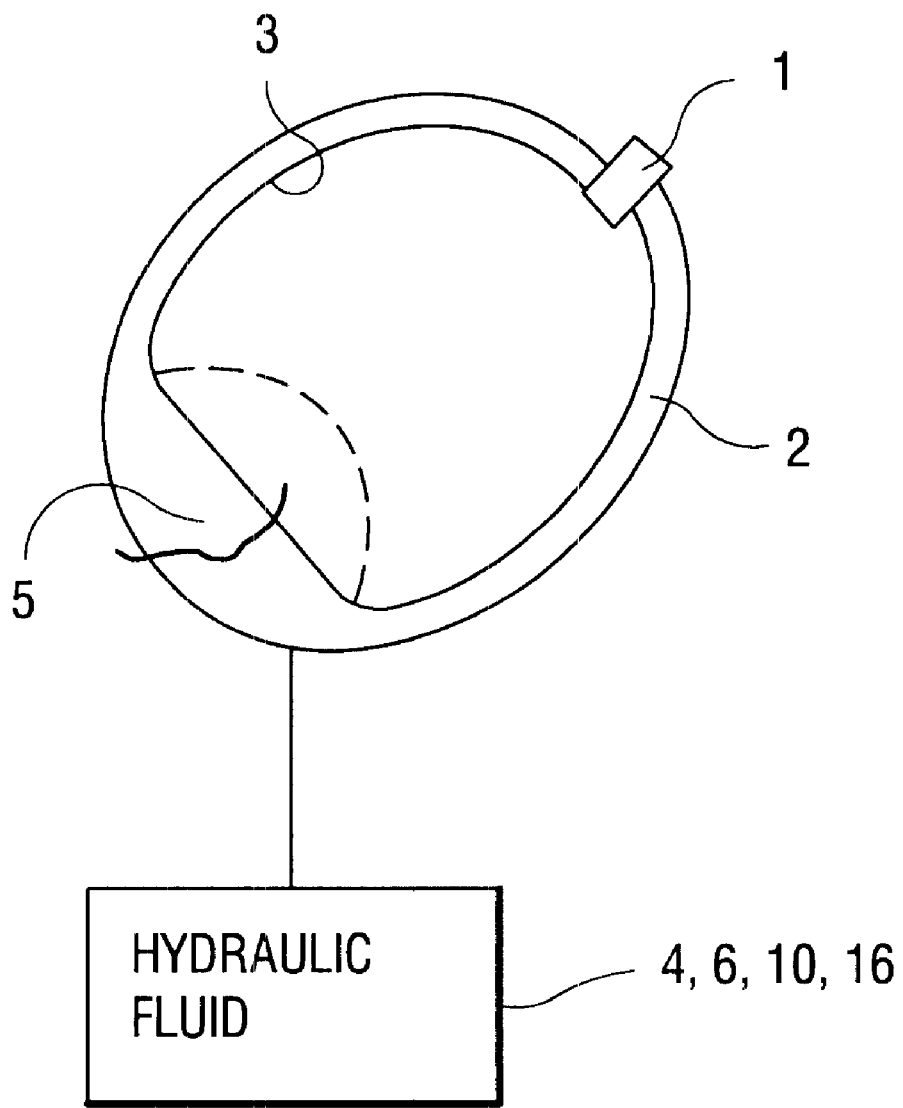
FIG. 8 is a schematic view of a band with a cavity defining a restriction opening for use in accordance with the invention.

FIGS. 1A–D is a block diagram of four different embodiments of the heartburn and reflux disease apparatus according to the invention. FIG. 1A shows an elongated restriction member in the form of a band 2 forming a loop which defines a restriction opening. The band 2 provides a restricted cross-sectional area of the food passageway in the stomach or esophagus when applied around the esophagus or stomach. FIG. 1A further shows a separate reservoir 4, a one way pump 6 and an alternate valve 8. FIG. 1B shows the band 2 and a fluid supply reservoir 10. FIG. 1C shows the band 2, a two way pump 12 and the reservoir 4. FIG. 1D shows a servo system with a first closed system controlling a second system. The servo system comprises the fluid supply reservoir 10 and a servo reservoir 14. The servo reservoir 14 controls a larger adjustable reservoir 16 which in connection with the band 2 applied around the stomach immediately close to the cardia or around the esophagus varies the volume of a cavity in the band, which in turn varies the restricted cross-sectional area of the food passageway. Such a band 2 forming the restriction opening 3 is illustrated schematically in FIG. 8. The band 2 comprises an adjustment device having an expandable/contractible cavity 5 which is expanded or contracted by supplying hydraulic fluid (e.g. from reservoir 4, 6,10, or 16), and the band 2 may be sutured in place, illustrated schematically at 7 in FIG. 8.

Figure 2A:
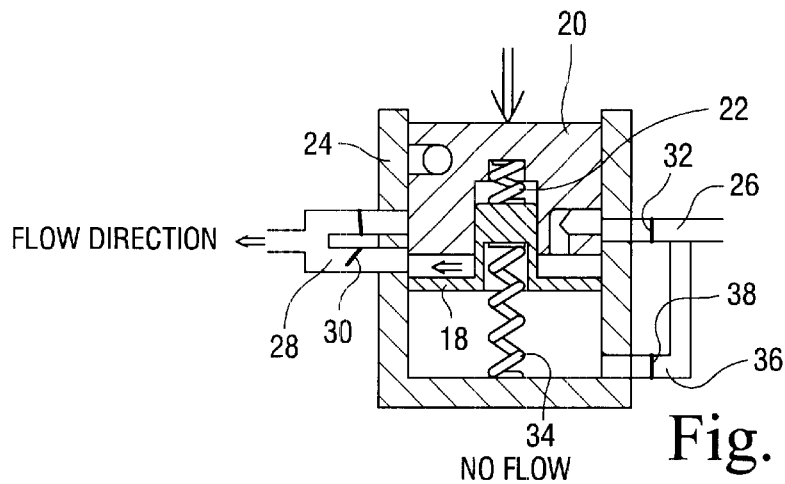
FIGS. 2A–D are cross-sectional views of a pump mechanism according to FIG. 1C, which is designed to pump fluid in opposite directions by mechanically pushing a wall portion in only one direction.
Figure 2B:
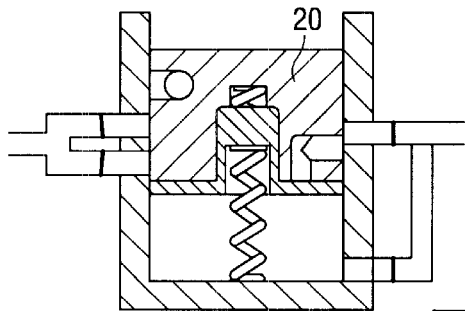
Figure 2C:
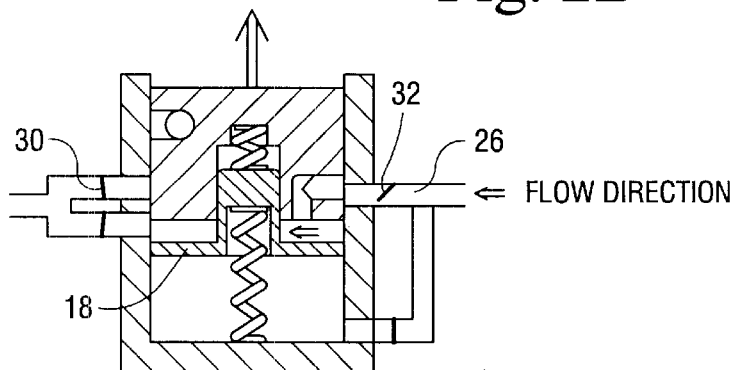
Figure 2D:
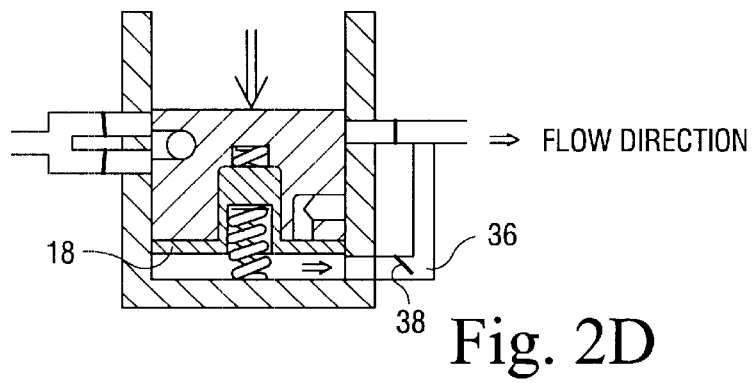

FIGS. 2A–D are cross-sectional views of a pump mechanism adapted to pump fluid in both directions only by mechanically pushing a separate sealing wall portion 18 in one direction. FIG. 2A shows a piston 20 pushed forwards against a spring 22 towards the wall portion 18 and located in a pump housing 24 conducting fluid from a right upper fluid passage 26 of the housing 24 to a left fluid passage 28 of the housing 24. A main valve 30 is open and a non-return valve 32 is closed. FIG. 2B illustrates the first pump movement in which the piston 20 has moved forwards and reaches the wall portion 18. FIG. 2C illustrates how the piston 20 moves backwards by the action of the spring 22. The main valve 30 is now closed and the non-return valve 32 is open for fluid from the right upper passage 26. FIG. 1D illustrates how the piston 20 is moved further downwards from its position according to FIG. 2B while pushing the wall portion 18 downwardly against a second spring 34 that is stronger than spring 22, whereby fluid escapes from a right lower fluid passage 36. When moving the piston 20 backwardly from the position according to FIG. 2D, fluid enters the left fluid passage 28 and a valve 38 in the lower right fluid passage 36 closes.

Figure 3:
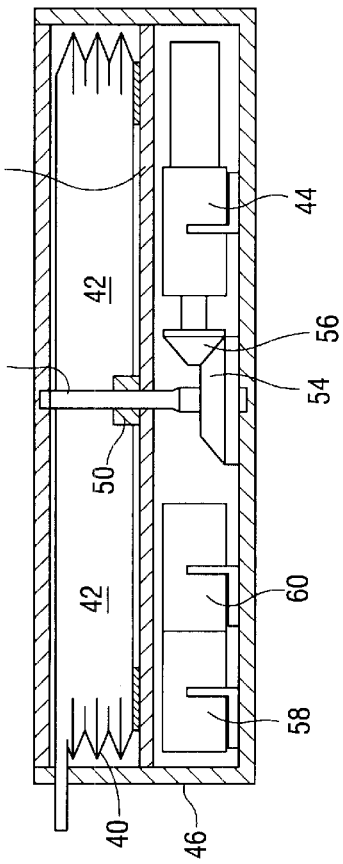
FIG. 3 is a cross-sectional view of a reservoir having a variable volume controlled by a remote control motor, in accordance with a particular embodiment of the principal embodiment shown in FIG. 1B or 2B.

FIG. 3 is a cross-sectional view of a reservoir 40 defining a chamber 42, the size of which is variable and is controlled by a remote controlled electric motor 44, in accordance with FIG. 1B or 1D. The reservoir 40 and the motor 44 are placed in a housing 46. The chamber 42 is varied by moving a large wall 48. The wall 48 is secured to a nut 50, which is threaded on a rotatable spindle 52. The spindle 52 is rotated by the motor 44 via an angular gearing, which comprises two conical gear wheels 54 and 56 in mesh with each other. The motor 44 is powered by a battery 58 placed in the housing 46. An signal receiver 60 for controlling the motor 44 is also placed in the housing 46. Alternatively, the battery 58 and the signal receiver 60 may be mounted in a separate place. The motor 44 may also be powered by energy transferred from transmitted signals.

Figure 4:
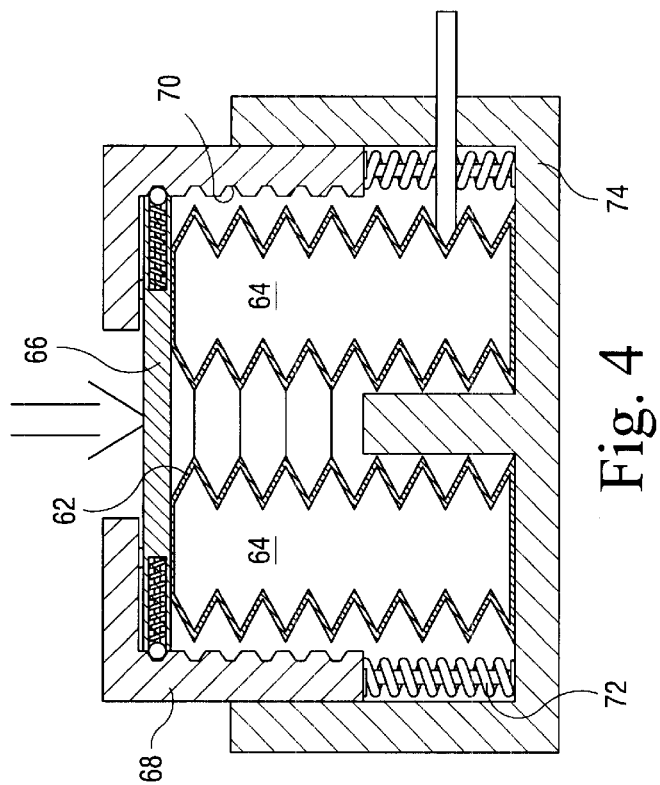
FIG. 4 is a cross-sectional view of a reservoir having a variable volume adjustable by manual manipulation, in accordance with a particular embodiment of the principal embodiment shown in FIG. 1B or 1D.

FIG. 4 is a cross-sectional view of a reservoir 62 defining a chamber 64, the size of which is variable and is controlled by manual manipulation. A gable wall portion 66 of an open ended inner cylindrical housing 68 is adapted to be pushed downwards to fit in a desired locking groove 70 of a plurality of locking grooves 70 on the mantle wall of the cylindrical housing 68, to reduce the size of the chamber 64. The inner cylindrical housing 68 is suspended by springs 72 and is telescopically applied on an outer cylindrical housing 74. When pushing the inner cylindrical housing 68 it moves downwards relative to the outer cylindrical housing 74 causing the gable wall portion 66 to release from the locking groove 70 and move upwards relative to the inner cylindrical housing 68. When the inner housing 68 is moved upwardly by the action of the springs 72 the size of the chamber 64 is increased.

FIGS. 5A and 5B show a servo means comprising a main ring-shaped fluid reservoir 76 defining a chamber 78, the size of which is variable. Centrally positioned in the main ring-shaped reservoir 76 there is a servo fluid reservoir 80 defining a chamber 82, the size of which is variable. The chamber 82 of the servo reservoir 80 is substantially smaller than the chamber 78 of the main reservoir 76. The two reservoirs 76 and 80 are situated between two opposite separate walls 84 and 86, and are secured thereto. When changing the amount of fluid in the servo reservoir 80, the two opposite walls 84,86 are moved towards or away from each other, whereby the size of the chamber 78 of the main reservoir 76 is changed.

Figure 6:
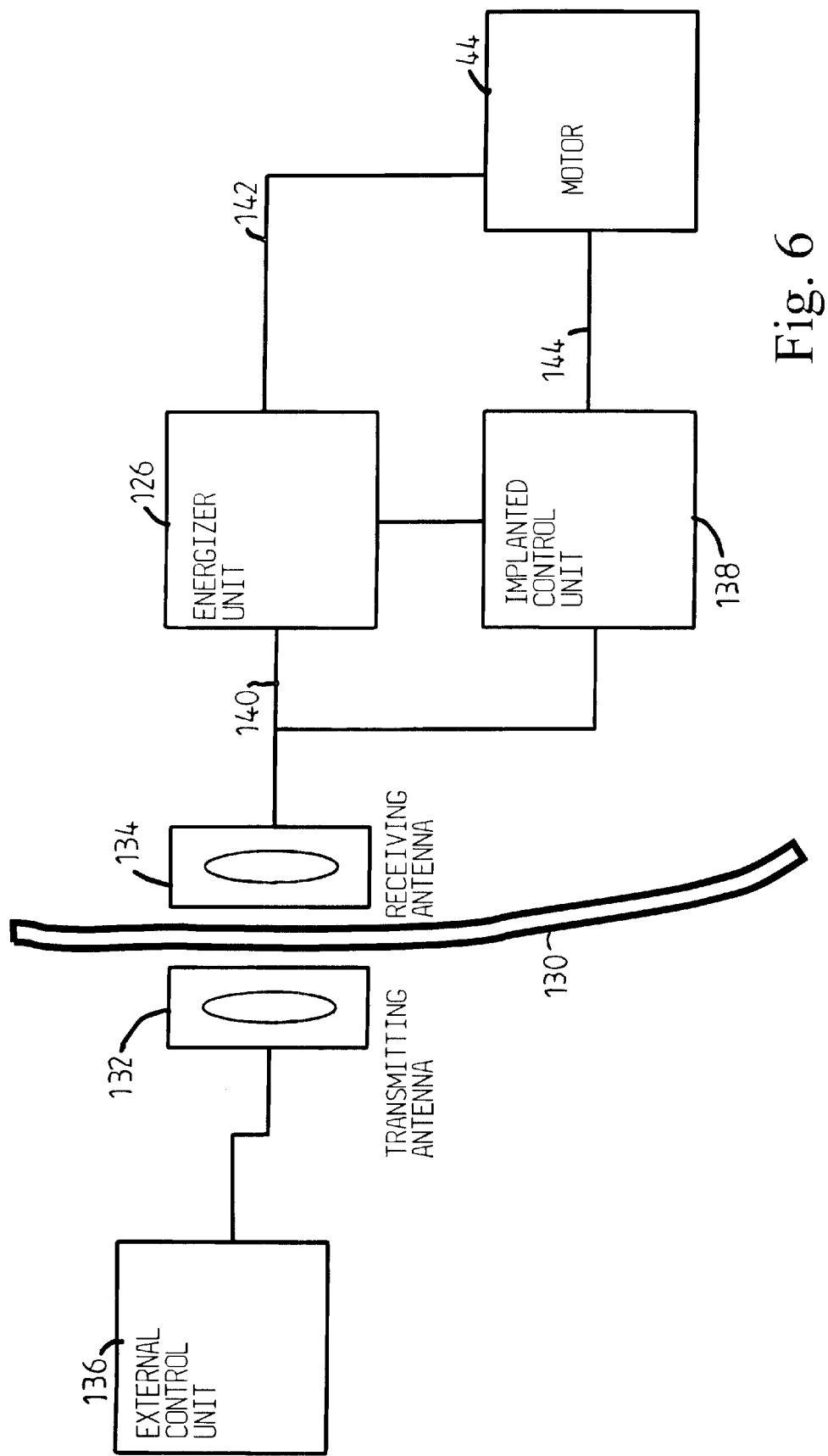
FIG. 6 is a block diagram illustrating remote control components of the device of the invention.

FIG. 6 shows the basic parts of a remote control system of the apparatus of the invention including the electric motor 44 of the embodiment shown in FIG. 3. In this case, the remote control system is based on the transmission of electromagnetic wave signals, often of high frequencies in the order of 100 kHz–1 gHz, through the skin 130 of the patient. In FIG. 6, all parts placed to the left of the skin 130 are located outside the human's or animal's body and all parts placed to the right of the skin 130 are implanted. Any suitable remote control system may be used.

An external signal transmitting antenna 132 is to be positioned close to a signal receiving antenna 134 implanted close to the skin 130. As an alternative, the receiving antenna 134 may be placed for example inside the abdomen of the patient. The receiving antenna 134 comprises a coil, approximately 1–100 mm, preferably 25 mm in diameter, wound with a very thin wire and tuned with a capacitor to a specific high frequency. A small coil is chosen if it is to be implanted under the skin of the patient and a large coil is chosen if it is to be implanted in the abdomen of the patient. The transmitting antenna 132 comprises a coil having about the same size as the coil of the receiving antenna 134 but wound with a thick wire that can handle the larger currents that is necessary. The coil of the transmitting antenna 132 is tuned to the same specific high frequency as the coil of the receiving antenna 134.

An external control unit 136 comprises a microprocessor, a high frequency electromagnetic wave signal generator and a power amplifier. The microprocessor of the control unit 136 is adapted to switch the generator on/off and to modulate signals generated by the generator to send digital information via the power amplifier and the antennas 132,134 to an implanted control unit 138. To avoid that accidental random high frequency fields trigger control commands, digital signal codes are used. A conventional keypad placed on the external control unit 136 is connected to the microprocessor thereof. The keypad is used to order the microprocessor to send digital signals to either increase or decrease the size of the restriction opening defined by the loop of the restriction member 2. The microprocessor starts a command by applying a high frequency signal on the antenna 132. After a short time, when the signal has energized the implanted parts of the control system, commands are sent to increase or decrease the size of the restriction opening of the restriction member 2 in predefined steps. The commands are sent as digital packets in the form illustrated below.

| Start pattern, 8 bits | Command, 8 bits | Count, 8 bits | Checksum, 8 bits |
| --- | --- | --- | --- |

The commands are sent continuously during a rather long time period (e.g. about 30 seconds or more). When a new increase or decrease step is desired the Count byte is increased by one to allow the implanted control unit 138 to decode and understand that another step is demanded by the external control unit 136. If any part of the digital packet is erroneous, its content is simply ignored.

Through a line 140, an implanted energizer unit 126 draws energy from the high frequency electromagnetic wave signals received by the receiving antenna 134. The energizer unit 126 stores the energy in a power supply, such as a large capacitor, powers the control unit 138 and powers the electric motor 44 via a line 142.

The control unit 138 comprises a demodulator and a microprocessor. The demodulator demodulates digital signals sent from the external control unit 136. The microprocessor of the control unit 138 receives the digital packet, decodes it and, provided that the power supply of the energizer unit 126 has sufficient energy stored, sends a signal via a signal line 144 to the motor 44 to either increase or decrease the size of the restriction opening of the restriction member 2 depending on the received command code.

Alternatively, the energy stored in the power supply of the energizer unit may only be used for powering a switch, and the energy for powering the motor 44 may be obtained from another implanted power source of relatively high capacity, for example a battery. In this case the switch is adapted to connect the battery to the control unit 138 in an on mode when the switch is powered by the power supply and to keep the battery disconnected from the control unit in a standby mode when the switch is unpowered.

Figure 7:
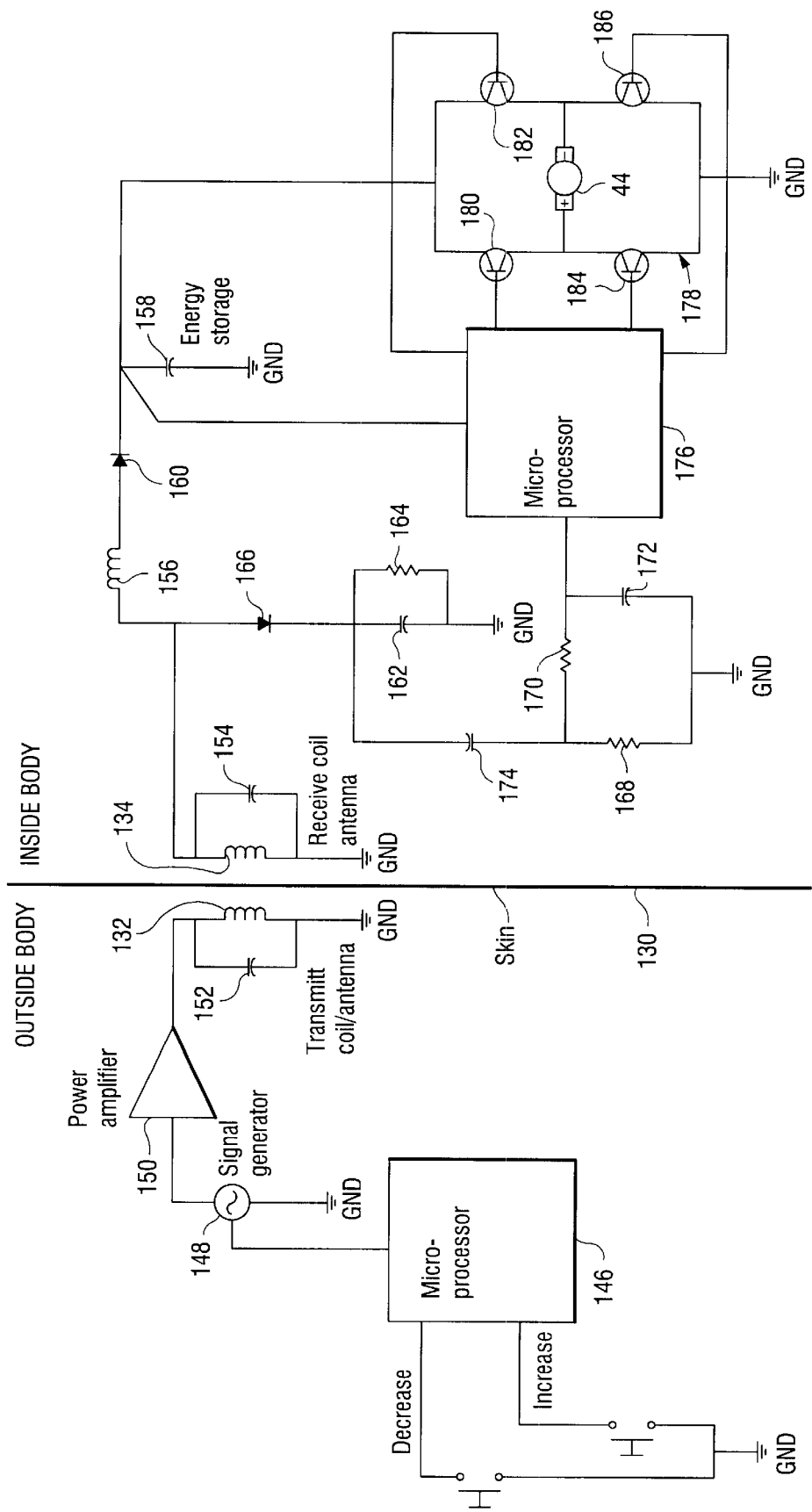
FIG. 7 is a schematic view of exemplary circuitry used for the block diagram in FIG. 4.

With reference to FIG. 7, the remote control system schematically described above will now be described in accordance with a more detailed embodiment. The external control unit 136 comprises a microprocessor 146, a signal generator 148 and a power amplifier 150 connected thereto. The microprocessor 146 is adapted to switch the signal generator 148 on/off and to modulate signals generated by the signal generator 148 with digital commands that are sent to implanted components of the apparatus. The power amplifier 150 amplifies the signals and sends them to the external signal transmitting antenna 132. The antenna 132 is connected in parallel with a capacitor 152 to form a resonant circuit tuned to the frequency generated by the signal generator 148.

The implanted signal receiving antenna coil 134 forms together with a capacitor 154 a resonant circuit that is tuned to the same frequency as the transmitting antenna 132. The signal receiving antenna coil 134 induces a current from the received high frequency electromagnetic waves and a rectifying diode 160 rectifies the induced current, which charges a storage capacitor 158. A coil 156 connected between the antenna coil 134 and the diode 160 prevents the capacitor 158 and the diode 160 from loading the circuit of the signal receiving antenna 134 at higher frequencies. Thus, the coil 156 makes it possible to charge the capacitor 158 and to transmit digital information using amplitude modulation.

A capacitor 162 and a resistor 164 connected in parallel and a diode 166 forms a detector used to detect amplitude modulated digital information. A filter circuit is formed by a resistor 168 connected in series with a resistor 170 connected in series with a capacitor 172 connected in series with the resistor 168 via ground, and a capacitor 174, one terminal of which is connected between the resistors 168, 170 and the other terminal of which is connected between the diode 166 and the circuit formed by the capacitor 162 and resistor 164. The filter circuit is used to filter out undesired low and high frequencies. The detected and filtered signals are fed to an implanted microprocessor 176 that decodes the digital information and controls the motor 44 via an H-bridge 178 comprising transistors 180,182,184 and 186. The motor 44 can be driven in two opposite directions by the H-bridge 178.

The microprocessor 176 also monitors the amount of stored energy in the storage capacitor 158. Before sending signals to activate the motor 44, the microprocessor 176 checks whether the energy stored in the storage capacitor 158 is enough. If the stored energy is not enough to perform the requested operation, the microprocessor 176 waits for the received signals to charge the storage capacitor 158 before activating the motor 44.

FIGS. 9A and 9B show an embodiment of the apparatus of the invention comprising a restriction device 202 having an elongated flexible restriction member 204, such as a belt, a cord or the like. The flexible member 204 extends in a loop around the esophagus 206 (or stomach). (Alternatively, the flexible member 204 may comprise two separate parts on opposite sides of the esophagus.) One portion 204A of member 204 is attached to a frame 208 and another portion 204B of member 204 opposite portion 204A in the loop of the flexible member 204 is connected to an adjustment device 210, which is fixed to the frame 208. The adjustment device 210 pulls the flexible member 204 in the direction from portion 204A to squeeze the esophagus between two opposite lengths of the flexible member 204 to thereby decrease the cross-sectional area in the esophagus (or stomach), see FIG. 96A, and releases the esophagus from the flexible member 204 to thereby increase the cross-sectional area in the esophagus 206, see FIG. 9B.

FIGS. 10A and 10B show an embodiment of the apparatus of the invention comprising a restriction device 212 having two plate or bar elements 214 on opposite sides of the esophagus 206 (or stomach). An adjustment device 216 moves the elements 212 in parallel towards each other to squeeze the esophagus 206 between the elements 212 to thereby decrease the cross-sectional area in the esophagus, see FIG. 10A, and moves the elements 212 away from each other to increase the cross-sectional area in the esophagus 206, see FIG. 10B.

FIG. 11 shows an embodiment of the apparatus of the invention comprising a restriction device 218 having two articulated clamping elements 220 positioned on opposite sides of the esophagus 206 (or stomach). An adjustment device 222 moves the clamping elements 220 toward each other to clamp the esophagus 206 between the clamping elements 220 to thereby decrease the cross-sectional area in the esophagus 206, and moves the clamping elements 420 away from each other to release the esophagus 206 from the clamping elements 220 to thereby increase the cross-sectional area in the esophagus 206.

FIGS. 12A, 12B and 12C show an embodiment of the apparatus of the invention comprising a restriction device 224 having three bending members in the form of cylindrical rollers 226, 228 and 230 displaced relative one another in a row along the esophagus 206 (or stomach) and positioned alternately on opposite sides of the esophagus 206. (Alternatively, each roller 226, 228 and 230 may take the shape of an hour-glass.) An adjustment device 232 moves the two outer rollers 226,230 laterally against the esophagus 206 in one direction and the intermediate roller 228 against the esophagus 206 in the opposite direction to bend the esophagus to thereby decrease the cross-sectional area in the esophagus 206, see FIG. 12B. To increase the cross-sectional area in the esophagus 206 the adjustment device 232 moves the rollers 226–230 away from the esophagus 206 to release the latter from the rollers 226–230, see FIG. 12C.

Figure 13A:
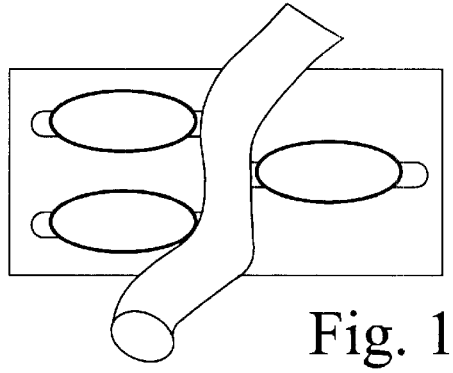
FIGS. 13A through 17B are five modifications of the embodiment of FIGS. 12A–12C.
Figure 13B:
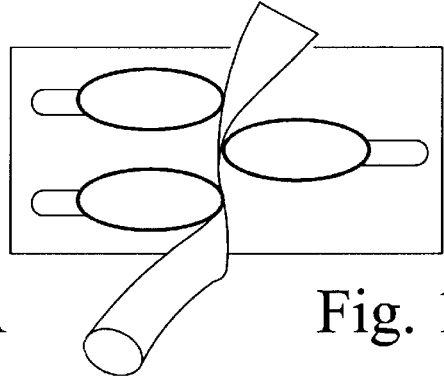
Figure 14A:
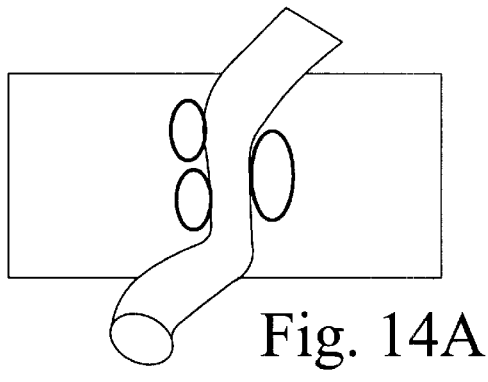
Figure 14B:
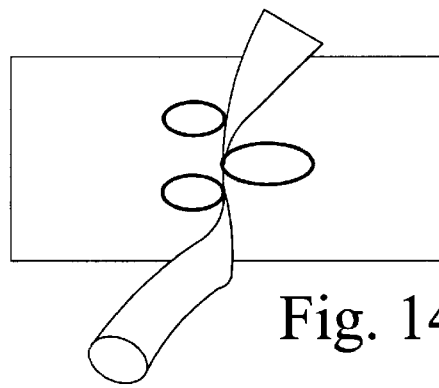
Figure 15A:
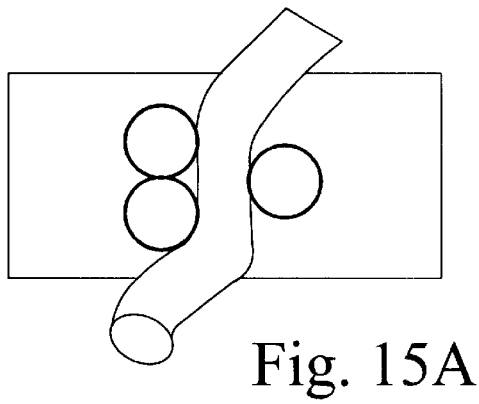
Figure 15B:
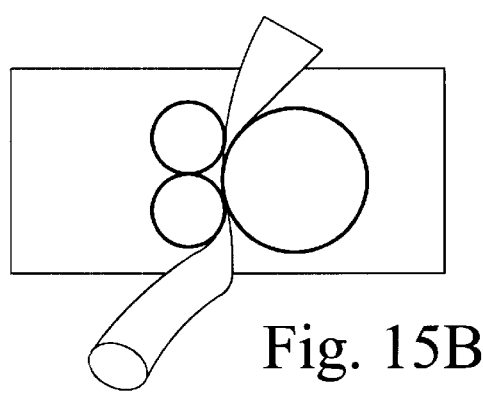
Figure 16A:
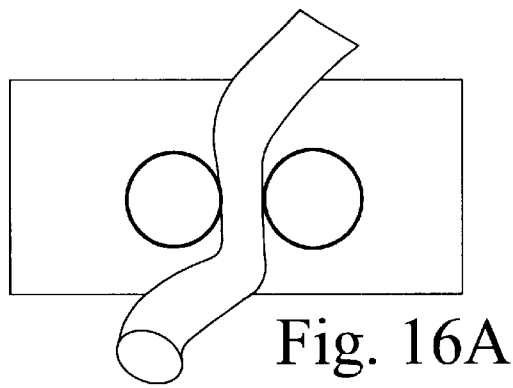
Figure 16B:
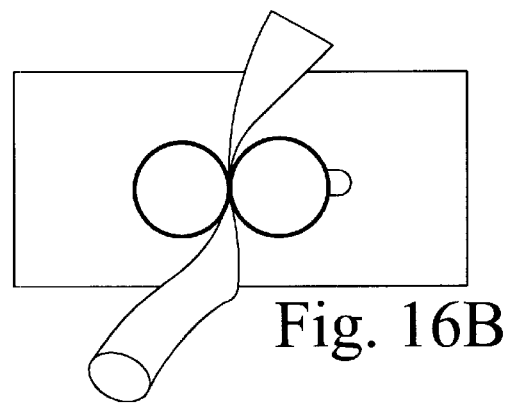
Figure 17A:
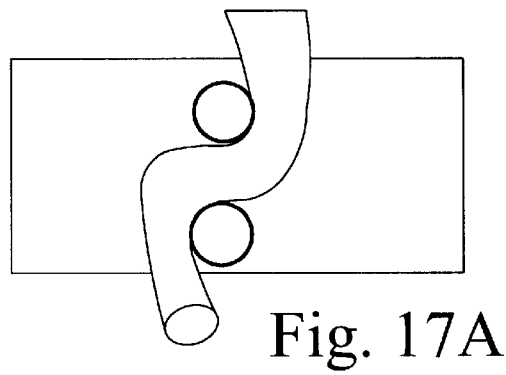
Figure 17B:
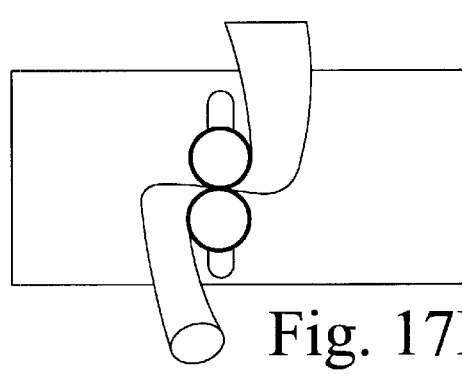

FIGS. 13A through 17B schematically illustrates modifications of the above embodiment according to FIGS. 12A–12C. Thus, FIGS. 13A and 13B show an embodiment similar to that of FIGS. 12A–12C except that the bending members are oval and not rotatable. FIGS. 14A and 14B show an embodiment similar to that of FIGS. 13A and 13B except that the oval bending members are rotatable to release the esophagus (or stomach), see FIG. 14A, and squeeze the esophagus, see FIG. 14B. FIGS. 15A and 15B show an embodiment similar to that of FIGS. 12A–12C except that the intermediate roller has a changeable diameter to release the esophagus (or stomach), see FIG. 15A, and squeeze the esophagus, see FIG. 15B. FIGS. 16A and 16B show an embodiment similar to that of FIGS. 110A–10C except that the elements are replaced by two cylindrical rollers positioned on opposite sides of the esophagus. Finally, FIGS. 17A and 17B show an embodiment substantially similar to that of FIGS. 16A and 16B except that the restriction device is turned 90° to form a S-shaped curvature of the esophagus.

Figure 18:
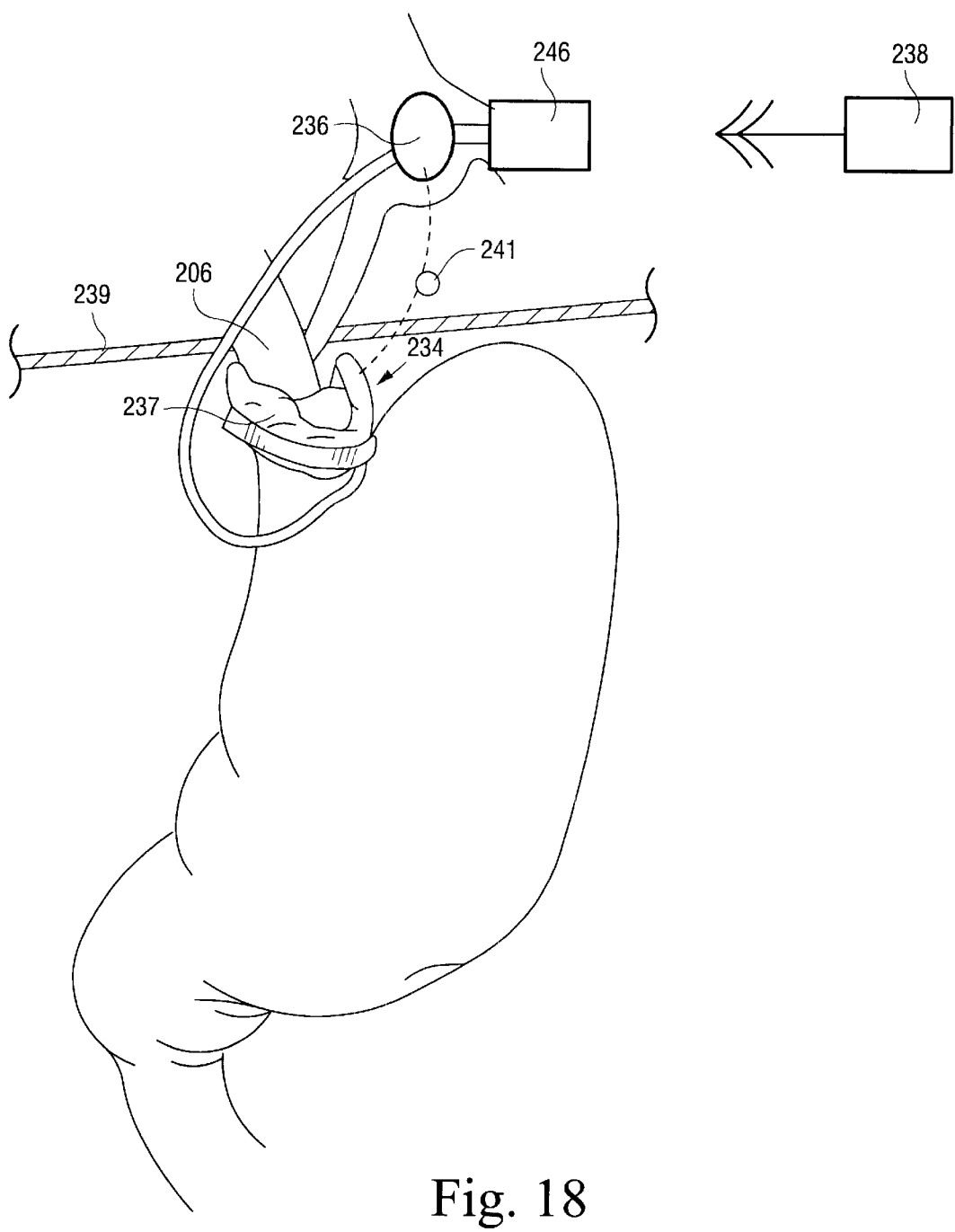
FIG. 18 illustrates an embodiment of the apparatus in accordance with the invention implanted in a patient and non-invasively controlled by a wireless remote control.

FIG. 18 illustrates an embodiment of the heartburn and reflux disease treatment apparatus of the invention implanted in a patient. Thus, an assembly of the apparatus implanted in the patient comprises an adjustable restriction device 234 engaging the esophagus 206 close to the cardia, an adjustment device (which may include an inflatable cavity in the restriction device) for adjusting the restriction device, and a unit 236 which includes a hydraulic operation device (which may include a pump) for operating the adjustment device and a fluid reservoir for supplying fluid to the operation device. The restriction device 234 is provided with a soft support member 237, which abuts upwardly against the diaphragm 239 of the patient. A wireless remote control of the apparatus comprises an external signal transmitter 238 and an implanted signal receiver 240, which includes a control unit for controlling the adjustment device of the implanted assembly in response to a control signal from the transmitter 238. The signal receiver 240 further includes an energizer unit which transfers energy from the control signal transmitted by the transmitter 238 into electric energy for energy consuming implanted components of the apparatus.

A pressure sensor 241 is implanted for sensing the pressure on the restriction device 234. The control unit of the signal receiver 240 controls the adjustment device to release the restriction device 234 in response to the pressure sensor 241 sensing an abnormal high pressure.

The embodiment according to FIG. 18 is particularly suited for patients that require regular adjustments of the restriction device during the day.

Figure 19:
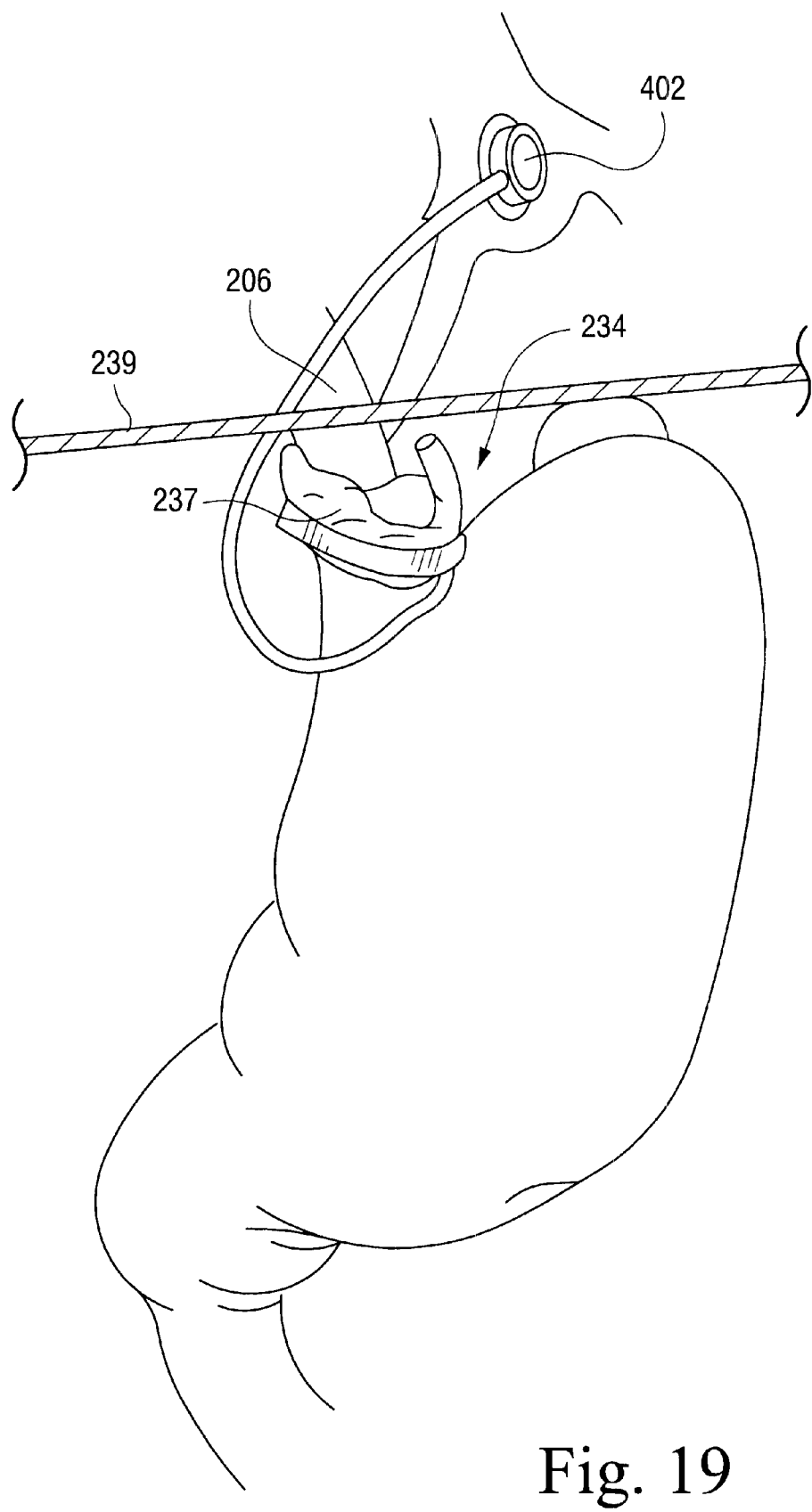
FIG. 19 illustrates another embodiment of the apparatus in accordance with the invention implanted in a patient and invasively adjustable.

FIG. 19 illustrates another embodiment of the heartburn and reflux disease treatment apparatus of the invention implanted in a patient. In this embodiment the restriction device 234 is provided with an expandable cavity, whereby the size of the restricted cross-sectional area of the food passageway is reduced upon expansion of the cavity and increased upon contraction of the cavity. An injection port 402 is implanted subcutaneously in the patient for transcutaneously adding fluid to and withdrawing fluid from the cavity of the restriction device 234 by the use of an injection needle. The embodiment according to FIG. 19 is particularly suited for patients that do not require frequent adjustments of the restriction device 234.

There are a number of conceivable alternative embodiments of the invention that give the same result as the above-described embodiments. For example, the microprocessor of the external and implanted, respectively, control units may be replaced by discrete components. The power amplifier of the external control unit may be omitted if the signals generated by the signal generator are strong enough. Therefore, the invention is to be accorded the broadest interpretation of the appended claims to encompass all equivalent structures and assemblies.

One further advantage with this invention is that there may be a night button on the remote control setting the adjustment device in a position with a larger stoma diameter during the night, thus avoiding vomiting or nausea.

In the practice of the present invention the details of the elongated restriction device (such as a gastric band) and the adjustment/operation device (which may have electric, hydraulic, or mechanical, etc. actuation), may be as described in copending applications Ser. No. 09/133,319, filed Aug. 13, 1998, Ser. No. 09/133,320, filed Aug. 13, 1998 and Ser. No. 09/133,322, filed Aug. 13, 1998, the disclosures of which are incorporated by reference herein.

The invention also comprises or consists of the foregoing structures and method steps, and is to be interpreted as broadly as allowed by the prior art.

What is claimed is:

1. A heartburn and reflux disease treatment apparatus, comprising:
   an adjustable restriction device adapted to be implanted in a patient having heartburn and reflux disease to engage the esophagus or the stomach close to the cardia without forming an upper pouch of the stomach that substantially accumulates food to form a restricted food passageway in the stomach or esophagus, said restriction device being designed to work like an artificial sphincter to allow food to readily pass through the passageway,
   an adjustment device adapted to be implanted in the patient for adjusting said restriction device to restrict the passageway sufficiently so as to substantially prevent regurgitation of stomach acids or foods into the patient's esophagus, and
   a hydraulic operation device adapted to be implanted in the patient for operating said adjustment device.

2. The apparatus according to claim 1, further comprising a reservoir adapted to be implanted in the patient and containing a predetermined amount of hydraulic fluid, wherein said hydraulic operation device operates said adjustment device by using said hydraulic fluid of said reservoir.

3. The apparatus according to claim 2, wherein said adjustment device comprises an expandable cavity in said restriction device, and said hydraulic operation device distributes hydraulic fluid from said reservoir to expand said cavity, and distributes hydraulic fluid from said cavity to said reservoir to contract said cavity, to thereby control the restriction of the food passageway, whereby the food passageway is restricted upon expansion of said cavity and enlarged upon contraction of said cavity when said restriction device is implanted.

4. The apparatus according to claim 3, wherein said reservoir defines a chamber for said predetermined amount of fluid and said hydraulic operation device changes the volume of said chamber.

5. The apparatus according to claim 4, wherein said hydraulic operation device comprises an injection port adapted to be implanted subcutaneously in the patient and in fluid communication with said chamber.

6. The apparatus according to claim 5, wherein said injection port is integrated in said reservoir.

7. The apparatus according to claim 4, wherein said hydraulic operation device comprises first and second wall portions of said reservoir, which are displaceable relative to each other to change the volume of said chamber of said reservoir.

8. The apparatus according to claim 7, wherein said first and second wall portions of said reservoir are displaceable relative to each other by manual manipulation thereof.

9. The apparatus according to claim 7, wherein said first and second wall portions of said reservoir are displaceable relative to each other by magnetic means, hydraulic means, or electric control means.

10. The apparatus according to claim 7, wherein said hydraulic operation device distributes fluid from said reservoir to said cavity in response to a predetermined first displacement of said first wall portion of said reservoir relative to said second wall portion of said reservoir and distributes fluid from said cavity to said reservoir in response to a predetermined second displacement of said first wall portion relative to said second wall portion.

11. The apparatus according to claim 3, wherein said hydraulic operation device comprise an activatable pump for pumping fluid between said reservoir and said cavity.

12. The apparatus according to claim 11, wherein said pump comprises a first activation member for activating said pump to pump fluid from said reservoir to said cavity and a second activation member for activating said pump to pump fluid from said cavity to said reservoir.

13. The apparatus according to claim 12, wherein said first and second activation members are operable by manual manipulation thereof.

14. The apparatus according to claim 12, wherein at least one of said activation members operates when subjected to a predetermined pressure external to the patient's body.

15. The apparatus according to claim 12, wherein at least one of said first and second activating members are operable by magnetic means, hydraulic means, or electric control means.

16. The apparatus according to claim 4, wherein said hydraulic operation device comprises a servo means.

17. The apparatus according to claim 16, wherein said hydraulic operation device comprises first and second wall portions of said reservoir, and said servo means provides relative displacement between said first and second wall portions of said reservoir to change the volume of said chamber of said reservoir.

18. The apparatus according to claim 17, wherein said servo means comprises magnetic means, or electric means.

19. The apparatus according to claim 17, wherein said servo means comprises hydraulic means.

20. The apparatus according to claim 19, wherein said servo means comprises a servo reservoir defining a chamber containing servo fluid, and said hydraulic operation device comprises first and second wall portions of said servo reservoir, which are displaceable relative to each other to change the volume of said chamber of said servo reservoir.

21. The apparatus according to claim 20, wherein said first and second wall portions of said servo reservoir are displaceable relative to each other by manual manipulation.

22. The apparatus according to claim 20, wherein said first and second wall portions of said servo reservoir are displaceable relative to each other by magnetic means, hydraulic means, or electric control means.

23. The apparatus according to claim 16, wherein said servo means comprises a servo reservoir and a fluid supply reservoir connected in a closed system and containing a further predetermined amount of fluid.

24. The apparatus according to claim 23, wherein said fluid supply reservoir defines a chamber for the further predetermined amount of fluid and said hydraulic operation device changes the volume of said chamber and thereby control the amount of fluid in said servo reservoir.

25. The apparatus according to claim 24, wherein said fluid supply reservoir comprises first and second wall portions, which are displaceable relative to each other to change the volume of said chamber of said fluid supply reservoir.

26. The apparatus according to claim 25, wherein said fluid supply reservoir increases the amount of fluid in said servo reservoir in response to a predetermined first displacement of said first wall portion of said fluid supply reservoir relative to said second wall portion of said fluid supply reservoir and desreases the amount of fluid in said servo reservoir in response to a predetermined second displacement of said first wall portion of said fluid supply reservoir relative to said second wall portion of said fluid supply reservoir.

27. The apparatus according to claim 3, further comprising a conduit providing fluid connection between said reservoir and said cavity, wherein said conduit and hydraulic operation device are devoid of any non-return valve to permit free flow of hydraulic fluid in both directions in said conduit.

28. The apparatus according to claim 27, wherein said reservoir forms a fluid chamber with a variable volume, and said hydraulic operation device distributes fluid from said chamber to said cavity by reduction of the volume of said chamber and withdraws fluid from said cavity by expansion of the volume of said chamber.

29. The apparatus according to claim 28, wherein said hydraulic operation device comprises a pump and a motor for driving said pump.

30. The apparatus according to claim 29, wherein said pump comprises a movable wall of said reservoir for changing the volume of said chamber.

31. The apparatus according to claim 29, wherein said motor is an electric motor.

32. The apparatus according to claim 1, wherein said restriction device comprises an elongated restriction member and forming means for forming said restriction member into at least a substantially closed loop around the esophagus or stomach, said loop defining a restriction opening, whereby said adjustment device adjusts said restriction member in said loop to change the size of said restriction opening.

33. The apparatus according to claim 32, wherein said forming means forms said restriction member into a loop having a predetermined size.

34. The apparatus according to claim 32, wherein said adjustment device changes the size of said restriction opening such that the outer circumferential confinement surface of said restriction member is changed.

35. The apparatus according to claim 32, wherein said adjustment device changes the size of said restriction opening such that the outer circumferential confinement surface of said restriction member is unchanged.

36. The apparatus according to claim 32, wherein said restriction member is non-inflatable, and said adjustment device mechanically adjusts said restriction member in said loop.

37. The apparatus according to claim 36, wherein said elongated restriction member is flexible, and said adjustment device pulls a first portion of said flexible restriction member from a second portion of said flexible restriction member opposite said first portion in said loop to squeeze the esophagus or stomach between two opposite lengths of said elongated flexible restriction member to restrict the passageway and moves said first portion toward said second portion of said restriction member to release the esophagus or stomach from said flexible restriction member to enlarge the passageway.

38. The apparatus according to claim 1, wherein said adjustment device mechanically adjusts said restriction device.

39. The apparatus according to claim 38, wherein said restriction device comprises two articulated clamping elements adapted to be positioned on opposite sides of the esophagus or stomach, and said adjustment device moves said clamping elements toward each other to clamp the esophagus or stomach between said clamping elements to restrict the passageway, and moves said clamping elements away from each other to release the esophagus or stomach from said elements to enlarge the passageway.

40. The apparatus according to claim 38, wherein said restriction device is adapted to bend a portion of the esophagus or stomach.

41. The apparatus according to claim 38, wherein said restriction device comprises at least two bending members adapted to be positioned on opposite sides of the esophagus or stomach displaced relative to each other along the food passageway in the esophagus or stomach, and said adjustment device moves said bending members toward each other to bend the esophagus or stomach between said bending members to restrict the passageway, and away from each other to release the esophagus or stomach from said bending members to enlarge the passageway.

42. The apparatus according to claim 41, wherein said bending members comprise rollers.

43. The apparatus according to claim 1, wherein said restriction device comprises at least two elements adapted to be positioned on different sides of the esophagus or stomach, and said adjustment device moves said elements toward each other to restrict the esophagus or stomach between said elements to restrict the passageway and moves said elements away from each other to release the esophagus or stomach from said elements to enlarge the passageway.

44. The apparatus according to claim 1, wherein said restriction device is adapted to bend a portion of the esophagus or stomach.

45. The apparatus according to claim 1, further comprising a wireless remote control for controlling said hydraulic operation device.

46. The apparatus according to claim 45, wherein said remote control comprises an external signal transmitter, receiver or transceiver and a signal receiver, transmitter or transceiver adapted to be implanted in the patient.

47. The apparatus according to claim 46, wherein said signal receiver comprises a control unit for controlling said hydraulic operation device in response to signals received from said signal transmitter.

48. The apparatus according to claim 47, further comprising an energizer unit adapted to be implanted in the patient for providing energy to energy consuming components of the apparatus adapted to be implanted in the patient.

49. The apparatus according to claim 48, further comprising a motor adapted to be implanted in the patient for operating said hydraulic operation device.

50. The apparatus according to claim 49, wherein said control unit powers said motor with energy provided by said energizer unit in response to signals received from said signal transmitter.

51. The apparatus according to claim 48, wherein said energizer unit transfers energy from said signals, as they are transmitted to said signal receiver, into electric energy.

52. The apparatus according to claim 47, wherein said energizer unit transfers the energy from said signals into direct or alternating current or a combination thereof.

53. The apparatus according to claim 46, wherein said signal transmitter and signal receiver transmit and receive signals in the form of digital pulses.

54. The apparatus according to claim 53, wherein said digital pulses comprise a magnetic field or an electric field.

55. The apparatus according to claim 46, wherein said signal transmitter and signal receiver transmit and receive wave signals.

56. The apparatus according to claim 55, wherein said wave signals comprise electromagnetic waves, sound waves or carrier waves for remote control signals or a combination thereof.

57. The apparatus according to claim 45, wherein said remote control comprises means for wireless transfer of energy from outside the patient's body to energy consuming implanted components of the apparatus adapted to be implanted in the patient.

58. The apparatus according to claim 57, further comprising a motor adapted to be implanted in the patient for operating said hydraulic operation device, wherein said means for wireless transfer of energy directly powers said motor with transferred energy.

59. The apparatus according to claim 58, wherein the energy transferred by said means for transfer of energy comprises wave signals.

60. The apparatus according to claim 58, wherein the energy transferred by said means for transfer of energy comprises an electric field or a magnetic field or a combination thereof.

61. The apparatus according to claim 45, wherein said remote control is capable of obtaining information correlated to implanted components of the apparatus adapted to be implanted in the patient and of commanding said adjustment device to adjust said restriction device in response to obtained information.

62. The apparatus according to claim 45, wherein said remote control is capable of obtaining information related to the food passageway in the stomach or esophagus and of commanding said adjustment device to adjust said restriction device in response to obtained information.

63. The apparatus according to claim 1, further comprising a control device for controlling said restriction device.

64. The apparatus according to claim 63, wherein said control device comprises an internal control unit implantable in the patient for controlling said restriction device.

65. The apparatus according to claim 64, wherein said internal control unit is programmable.

66. The apparatus according to claim 65, wherein said control device comprises an external control unit outside the patient's body, said internal control unit being programmable by said external control unit.

67. The apparatus according to claim 63, wherein said control device comprises an external control unit outside the patient's body for wirelessly controlling said restriction device.

68. The apparatus according to claim 67, wherein said external control unit is programmable.

69. The apparatus according to claim 1, further comprising at least one implantable sensor for sensing at least one physical parameter of the patient.

70. The apparatus according to claim 69, wherein said sensor directly or indirectly senses as said physical parameter the horizontal position of the patient.

71. The apparatus according to claim 69, wherein said sensor directly or indirectly senses as said physical parameter the pressure against said restriction device.

72. The apparatus according to claim 71, wherein said adjustment device is adapted to adjust said restriction device to enlarge the food passageway in response to said sensor sensing a predetermined pressure.

73. The apparatus according to claim 69, further comprising a control device for controlling said restriction device in response to signals from said sensor.

74. The apparatus according to claim 73, wherein said control device comprises an internal control unit implantable in the patient for directly controlling said restriction device in response to signals from said sensor.

75. The apparatus according to claim 73, wherein said control device comprises an external control unit outside the patient's body for controlling said restriction device in response to signals from said sensor.

76. The apparatus according to claim 1, wherein said hydraulic operation device non-invasively operates said adjustment device.

77. The apparatus according to claim 1, wherein said adjustment device comprises an expandable cavity in said restriction device, and said hydraulic operation device comprises an injection port implantable subcutaneously in the patient for transcutaneous supply of fluid to and withdrawal of fluid from said cavity, whereby the food passageway is restricted upon expansion of said cavity and enlarged upon contraction of said cavity when said restriction device is implanted.

78. The apparatus according to claim 1, further comprising a holding device adapted to be implanted in the patient to hold the esophagus or stomach in a position where the left and right crus muscles are located, to prevent the region of the cardia from moving through the diaphragm muscle.

79. The apparatus according to claim 1, wherein said operation device operates said adjustment device to adjust said restriction device to open and close the food passageway, when said restriction device engages the patient's stomach or esophagus.

80. The apparatus according to claim 79, wherein said operation device operates said adjustment device to steplessly adjust said restriction device.

81. The apparatus according to claim 1, wherein said operation device uses hydraulic fluid, the viscosity of which changes when said hydraulic fluid is exposed to energy different from thermal energy.

82. The apparatus according to claim 81, wherein the viscosity of said hydraulic fluid changes when said fluid is exposed to electric energy.

83. The apparatus according to claim 1, wherein said operation device and/or other energy consuming components of the apparatus are adapted to be energised with wirelessly transmitted energy from outside the patient's body.

84. The apparatus according to claim 1, further comprising an implantable battery or accumulator for energizing said operation device and/or other energy consuming components of the apparatus, wherein the energy from said battery or accumulator is releasable from outside the patient's body.

85. The apparatus according to claim 1, wherein said adjustment device adjusts said restriction device in a non-thermal manner.

86. The apparatus according to claim 1, wherein said adjustment device adjusts said restriction device in a non-manual manner.

87. The apparatus according to claim 1, wherein said adjustment device adjusts said restriction device in a non-magnetic manner.

88. The apparatus according to claim 1, wherein said hydraulic operation device is powered.

89. A heartburn and reflux disease treatment apparatus, comprising:

an adjustable restriction device adapted to be implanted in a patient having heartburn and reflux disease to engage the esophagus or the stomach close to the cardia without forming an upper pouch of the stomach that substantially accumulates food to form a restricted food passageway in the stomach or esophagus, said restriction device being designed to work like an artificial sphincter to allow food to readily pass through the passageway, an adjustment device adapted to be implanted in the patient for adjusting said restriction device to restrict the passageway sufficiently so as to substantially prevent regurgitation of stomach acids or foods into the patient's esophagus, wherein said adjustment device comprises servo means.

90. A heartburn and reflux disease treatment apparatus, comprising:

an adjustable restriction device adapted to be implanted in a patient having heartburn and reflux disease to engage the esophagus or the stomach close to the cardia without forming an upper pouch of the stomach that substantially accumulates food to form a restricted food passageway in the stomach or esophagus, said restriction device being designed to work like an artificial sphincter to allow food to readily pass through the passageway, an adjustment device adapted to be implanted in the patient for adjusting said restriction device to restrict the passageway sufficiently so as to substantially prevent regurgitation of stomach acids or foods into the patient's esophagus, and an electrically powered operation device for operating said adjustment device.

91. A method of treating a human or animal having heartburn and reflux disease, comprising:

(a) surgically implanting in the abdomen of the human or animal an adjustable restriction device which restricts a food passageway in the esophagus or the stomach close to the cardia without forming an upper pouch of the stomach that substantially accumulates food, and (b) from time to time, adjusting the restriction device so as (i) to enlarge the restricted passageway to allow food to readily pass therethrough into the human's or animal's stomach, or to allow the human or animal to regurgitate, or (ii) to restrict the restricted passageway sufficiently so as to substantially prevent regurgitation of stomach acids and foods into the esophagus.

92. A method as recited in claim 91, wherein the restriction device comprises a cavity which is expandable and contractable by the supply of hydraulic fluid thereto; and wherein (a) is practiced in part by implanting in the human or animal a reservoir containing a predetermined amount of hydraulic fluid and connecting the reservoir to the cavity and a hydraulic operation device for distributing fluid from the reservoir to the cavity; and wherein (b) is practiced by controlling the hydraulic operation device from a point outside the human's or animal's body without physically penetrating the human's or animal's body.

93. A method as recited in claim 91, wherein the restriction device comprises a cavity which is expandable and contractable by the supply of hydraulic fluid thereto; and wherein (a) is practiced in part by subcutaneously implanting in the human or animal an injection port connected to the cavity of the restriction device; and wherein (b) is practiced by injecting fluid through the injection port to expand the cavity to restrict the passageway and by withdrawing fluid from the injection port to contract the cavity to enlarge the passageway.

94. A method as recited in claim 91, wherein the restriction device is acted upon by an adjustment device which mechanically adjusts the restriction of the food passageway; and wherein (a) is practiced in part by implanting in the human or animal the adjustment device, implanting a reservoir containing a predetermined amount of hydraulic fluid and connecting the reservoir to the cavity, and implanting a hydraulic operation device for distributing fluid from the reservoir to the cavity; and wherein (b) is practiced by controlling the hydraulic operation device from a point outside the human or animal's body without physically penetrating the human's or animal's body to control the adjustment device so that the restriction of the food passageway is changed.

95. A method as recited in claim 91, wherein (a) is practiced by: (i) inflating the human's or animal's abdomen with gas by penetration of the human's or animal's skin, (ii) introducing at least two laparascopic trocars into the abdomen to introduce the restriction device and one or more medical instruments, and then (iii) applying the restriction device on the esophagus or stomach.

96. A method of treating a human or animal having heartburn and reflux disease, comprising the steps of:

a) placing at least two laparoscopic trocars within the human's or animal's body, b) using a dissecting tool inserted through the laparoscopic trocar, dissecting the region of the esophagus or stomach, c) introducing a restriction device of the apparatus through the trocars, d) placing the restriction device in engagement with the esophagus or the stomach close to the cardia without forming an upper pouch of the stomach that substantially accumulates food to create a restricted stoma, and e) from time to time, adjusting the restriction device so as (i) to enlarge the restricted stoma to allow food to readily pass therethrough into the human's or animal's stomach, or to allow the human or animal to regurgitate, or (ii) to restrict the restricted stoma sufficiently so as to substantially prevent regurgitation of stomach acids and foods into the esophagus.

97. A heartburn and reflux disease treatment apparatus, comprising:

an adjustable restriction device adapted to be implanted in a patient having heartburn and reflux disease to engage the esophagus or the stomach close to the cardia without forming an upper pouch of the stomach that substantially accumulates food to form a restricted food passageway in the stomach or esophagus, said restriction device being designed to work like an artificial sphincter to allow food to readily pass through the passageway, an adjustment device implantable in the patient for adjusting said restriction device to restrict the passageway sufficiently so as to substantially prevent regurgitation of stomach acids or foods into the patient's esophagus, and a holding device adapted to be implanted in the patient to hold the esophagus or stomach in a position where the left and right crus muscles are located, to prevent the region of the cardia from moving through the diaphragm muscle.

98. The apparatus according to claim 97, further comprising a wireless remote control for controlling said operation device.

99. The apparatus according to claim 97, further comprising a motor implantable in the patient for operating said operation device.

100. The apparatus according to claim 97, wherein said operation device non-invasively operates said adjustment device.

101. The apparatus according to claim 97, further comprising an implantable battery or accumulator for energizing said adjustment device or other energy consuming components of the apparatus, wherein the energy from said battery or accumulator is released from outside the patient's body.

102. The apparatus according to claim 101, wherein said adjustment device adjusts said restriction device in a non-thermal manner.

103. The apparatus according to claim 101, wherein said adjustment device adjusts said restriction device in a non-magnetic manner.

104. The apparatus according to claim 101, wherein said operation device is powered.

105. The apparatus according to claim 104, wherein said operation device is electrically powered.

106. The apparatus according to claim 97, further comprising an internal control unit implantable in the patient for controlling said restriction device.

107. The apparatus according to claim 97, further comprising at least one implantable sensor for sensing at least one physical parameter of the patient.

108. The apparatus according to claim 97, wherein said restriction device comprises an elongated restriction member adapted to be formed into a loop having a predetermined size.

109. The apparatus according to claim 97, wherein said operation device and/or other energy consuming components of the apparatus are adapted to be energised with wirelessly transmitted energy from outside the patient's body.

110. The apparatus according to claim 97, further comprising an implantable battery or accumulator for energizing said operation device and/or other energy consuming components of the apparatus, wherein the energy from said battery or accumulator is releasable from outside the patient's body.

111. The apparatus according to claim 110, further comprising an energy transmission device for transmitting wireless energy and an implantable energy transfer device adapted to transfer said wireless energy into an energy form suited for charging said battery or accumulator.

112. A heartburn and reflux disease treatment apparatus, comprising:

an adjustable restriction device adapted to be implanted in a patient having heartburn and reflux disease to engage the esophagus or the stomach close to the cardia without forming an upper pouch of the stomach that substantially accumulates food to form a restrictable food passageway in the stomach or esophagus, an adjustment device implantable in the patient for adjusting said restriction device, and an operation device implantable in the patient for operating said adjustment device to adjust said restriction device to open the passageway to allow food to readily pass through the passageway and close the passageway to prevent regurgitation of stomach acids or foods into the patient's esophagus, when said restriction device engages the patient's stomach or esophagus.

113. The apparatus according to claim 112, wherein said operation device operates said adjustment device to steplessly adjust said restriction device.

* * * * *